United States Patent
Kamei et al.

(10) Patent No.: US 10,590,389 B2
(45) Date of Patent: Mar. 17, 2020

(54) ENDODERMAL CELL PRODUCTION METHOD, LIVER CELL PRODUCTION METHOD, PANCREATIC CELL PRODUCTION METHOD, ENDODERMAL CELL INDUCTION PROMOTER, LIVER CELL INDUCTION PROMOTING KIT, PANCREATIC CELL INDUCTION PROMOTING KIT, AND MICROFLUIDIC DEVICE

(71) Applicant: Kyoto University, Kyoto-shi, Kyoto (JP)

(72) Inventors: Kenichiro Kamei, Kyoto (JP); Momoko Honda, Kyoto (JP)

(73) Assignee: Kyoto University, Kyoto (JP)

( * ) Notice: Subject to any disclaimer, the term of this patent is extended or adjusted under 35 U.S.C. 154(b) by 140 days.

(21) Appl. No.: 15/539,546

(22) PCT Filed: Dec. 22, 2015

(86) PCT No.: PCT/JP2015/085894
§ 371 (c)(1),
(2) Date: Jun. 23, 2017

(87) PCT Pub. No.: WO2016/104541
PCT Pub. Date: Jun. 30, 2016

(65) Prior Publication Data
US 2017/0362568 A1    Dec. 21, 2017

(30) Foreign Application Priority Data

Dec. 24, 2014 (JP) .................................. 2014-261088

(51) Int. Cl.
| | | |
|---|---|---|
| *C12N 5/071* | (2010.01) | |
| *C12M 1/00* | (2006.01) | |
| *C12M 3/00* | (2006.01) | |
| *C12N 15/09* | (2006.01) | |
| *C12N 5/073* | (2010.01) | |

(52) U.S. Cl.
CPC .............. *C12N 5/067* (2013.01); *C12M 1/00* (2013.01); *C12M 3/00* (2013.01); *C12N 5/0603* (2013.01); *C12N 5/0676* (2013.01); *C12N 15/09* (2013.01); *C12N 2501/119* (2013.01); *C12N 2501/15* (2013.01); *C12N 2501/155* (2013.01); *C12N 2501/16* (2013.01); *C12N 2501/727* (2013.01); *C12N 2501/999* (2013.01); *C12N 2506/00* (2013.01); *C12N 2506/02* (2013.01); *C12N 2533/54* (2013.01); *C12N 2533/90* (2013.01)

(58) Field of Classification Search
CPC ........................ C12N 2506/00; C12N 2506/02; C12N 5/067; C12N 5/0672; C12N 5/0603
See application file for complete search history.

(56) References Cited

U.S. PATENT DOCUMENTS

| | | |
|---|---|---|
| 2006/0276420 A1 | 12/2006 | Keller et al. |
| 2007/0281355 A1 | 12/2007 | Dalton et al. |
| 2010/0144033 A1 | 6/2010 | Mandalam et al. |
| 2011/0151561 A1 | 6/2011 | Davis et al. |
| 2012/0149110 A1 | 6/2012 | Kitamura et al. |
| 2013/0156743 A1 | 6/2013 | Vallier et al. |
| 2013/0164266 A1 | 6/2013 | Jensen |
| 2014/0271566 A1 | 9/2014 | Agulnick |
| 2014/0329321 A1 | 11/2014 | Rajesh et al. |

FOREIGN PATENT DOCUMENTS

| | | |
|---|---|---|
| EP | 2 671 944 | 11/2013 |
| JP | 2008-509676 | 4/2008 |
| JP | 2008-546414 | 12/2008 |
| JP | 2013-515481 | 5/2013 |
| JP | 2013-150613 | 8/2013 |
| JP | 2013-532966 | 8/2013 |
| JP | 2013-535980 | 9/2013 |
| WO | 2011/021558 | 2/2011 |
| WO | 2012/105505 | 8/2012 |
| WO | 2013/174794 | 11/2013 |

OTHER PUBLICATIONS

Hannan et al., "Production of hepatocyte like cells from human pluripotent stem cells", Nat Protoc., vol. 8, No. 2, pp. 430-437 (2013).
Chayosumrit et al., "Alginate microcapsule for propagation and directed differentiation of hESCs to definitive endoderm", Biomaterials, vol. 31, pp. 505-514 (2009) and supplementary data.
Sivasubramaniyan et al., "Rho Kinase Inhibitor Y27632 Alters the Balance Between Pluripotency and Early Differentiation Events in Human Embryonic Stem Cells", Current Stem Cell Research & Therapy, vol. 5, pp. 2-12 (2010).
Ramasamy et al., "Application of Three-Dimensional Culture Conditions to Human Embryonic Stem Cell-Derived Definitive Endoderm Cells Enhances Hepatocyte Differentiation and Functionality", Tissue Engineering:Part A, vol. 19, No. 3 & 4, pp. 360-367 (2013).
Extended European Search Report issued in corresponding European Patent Application No. 15873109.1, dated Jul. 6, 2018, 9 pages.

(Continued)

*Primary Examiner* — Christopher Adam Hixson
(74) *Attorney, Agent, or Firm* — Hamre, Schumann, Mueller & Larson, P.C.

(57) ABSTRACT

The present invention provides an endodermal cell production method that can induce differentiation of pluripotent cells into endodermal cells even when the pluripotent cells are dispersed and can achieve improved endodermal cell production efficiency. The endodermal cell production method according to the present invention is a method for producing endodermal cells by inducing differentiation of pluripotent cells into the endodermal cells, including the step of: inducing differentiation of the pluripotent cells into the endodermal cells in the presence of an endodermal cell inducing factor. In the induction step, the cell density of the pluripotent cells at the start of the induction preferably is from $0.5 \times 10^4$ to $2 \times 10^4$ cells/cm$^2$.

20 Claims, 8 Drawing Sheets

Specification includes a Sequence Listing.

(56) References Cited

OTHER PUBLICATIONS

Tahamtani et al., "Treatment of Human Embryonic Stem Cells with Different Combinations of Priming and Inducing Factors Toward Definitive Endoderm", Stem Cells and Development, vol. 22, No. 9, May 1, 2013, pp. 1419-1432.

Watanabe, et al., A ROCK inhibitor permits survival of dissociated human embryonic stem cells, Nature Biotechnology, vol. 25, No. 6, Jun. 1, 2007, pp. 681-686.

Sekine, et al., "Highly Efficient Generation of Definitive Endoderm Lineage from Human Induced Pluripotent Stem Cells", Transplantation Proceedings, vol. 44, No. 4, Jan. 1, 2012, pp. 1127-1129.

Lu, et al., "Small molecules and small molecule drugs in regenerative medicine" Drug Discovery Today, vol. 19, No. 6, Jun. 1, 2014, pp. 801-808.

Nii, et al., "Analysis of essential pathways for self-renewal in common marmoset embryonic stem cells", FEBS Open Bio, vol. 4, No. 1, Jan. 1, 2014, pp. 213-219.

Kamei, et al., "Three-dimensional cultured Liver-on-a-Chip with mature hepatocyte-like cells derived from human pluripotent stem cells" bioRxiv, May 17, 2018—Retrieved from the Internet: https://www.biorxiv.org/content/biorxiv/early/2018/05/17/232215.full.pdf.

SEQUENCE LISTING

```
<160> NUMBER OF SEQ ID NOS: 32

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
cgcacggaat ttgaacagta                                              20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
ggatcaggga cctgtcacac                                              20

<210> SEQ ID NO 3
<211> LENGTH: 20
<212> TYPE: DNA
<213> ORGANISM: Artificial Sequence
<220> FEATURE:
<223> OTHER INFORMATION: primer
```

-continued

```
<400> SEQUENCE: 3
accacagtcc atgccatcac                                          20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
tccaccaccc tgttgctgta                                          20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
aaatgcgttt ctcgttgctt                                          20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
gccacaggcc aatagtttgt                                          20

<210> SEQ ID NO 7
<211> LENGTH: 19
<212> TYPE: DNA
<213> ORGANISM: Artificial Sequence
<220> FEATURE:
<223> OTHER INFORMATION: primer

<400> SEQUENCE: 7
ccacgggcaa acactacgg                                           19

<210> SEQ ID NO 8
<211> LENGTH: 19
<212> TYPE: DNA
<213> ORGANISM: Artificial Sequence
<220> FEATURE:
<223> OTHER INFORMATION: primer

<400> SEQUENCE: 8
ggcaggctgc tgtcctcat                                           19

<210> SEQ ID NO 9
<211> LENGTH: 23
<212> TYPE: DNA
<213> ORGANISM: Artificial Sequence
<220> FEATURE:
<223> OTHER INFORMATION: primer

<400> SEQUENCE: 9
acctgaatga gaagttctac agc                                      23

<210> SEQ ID NO 10
<211> LENGTH: 22
```

```
<212> TYPE: DNA
<213> ORGANISM: Artificial Sequence
<220> FEATURE:
<223> OTHER INFORMATION: primer

<400> SEQUENCE: 10
ctggggttca tcaccaaata ca                                            22

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
ccctggatcc agatctgcaa                                               20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
tgcttgtcgt ctctgtccca                                               20

<210> SEQ ID NO 13
<211> LENGTH: 22
<212> TYPE: DNA
<213> ORGANISM: Artificial Sequence
<220> FEATURE:
<223> OTHER INFORMATION: primer

<400> SEQUENCE: 13
ggtgctgcat ggatatgaag tg                                            22

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
tggatccagg gggtgcttac                                               20

<210> SEQ ID NO 15
<211> LENGTH: 21
<212> TYPE: DNA
<213> ORGANISM: Artificial Sequence
<220> FEATURE:
<223> OTHER INFORMATION: primer

<400> SEQUENCE: 15
acctccaaca ggtggcttgc a                                             21

<210> SEQ ID NO 16
<211> LENGTH: 23
<212> TYPE: DNA
<213> ORGANISM: Artificial Sequence
<220> FEATURE:
<223> OTHER INFORMATION: primer

<400> SEQUENCE: 16
```

```
acaccaatct tctccatgct acc                                    23

<210> SEQ ID NO 17
<211> LENGTH: 24
<212> TYPE: DNA
<213> ORGANISM: Artificial Sequence
<220> FEATURE:
<223> OTHER INFORMATION: primer

<400> SEQUENCE: 17
gtgctgagta agattcagca tggg                                   24

<210> SEQ ID NO 18
<211> LENGTH: 25
<212> TYPE: DNA
<213> ORGANISM: Artificial Sequence
<220> FEATURE:
<223> OTHER INFORMATION: primer

<400> SEQUENCE: 18
agcatgtcat cttcagttgc atcct                                  25

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
gtgcctttat cacccatgct                                        20

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
tcttggattt gtgggctttc                                        20

<210> SEQ ID NO 21
<211> LENGTH: 22
<212> TYPE: DNA
<213> ORGANISM: Artificial Sequence
<220> FEATURE:
<223> OTHER INFORMATION: primer

<400> SEQUENCE: 21
acatttaccc aaactgtcca tt                                     22

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
gcttcagtcc ctttctcgtc                                        20

<210> SEQ ID NO 23
<211> LENGTH: 20
<212> TYPE: DNA
<213> ORGANISM: Artificial Sequence
```

```
<220> FEATURE:
<223> OTHER INFORMATION: primer

<400> SEQUENCE: 23
gacggctgtc atacagagca                                                 20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
cgcaggtagt gatagcctga                                                 20

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
ttggcacaat gaagtgggta                                                 20

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
aaaggcaatc aacaccaagg                                                 20

<210> SEQ ID NO 27
<211> LENGTH: 18
<212> TYPE: DNA
<213> ORGANISM: Artificial Sequence
<220> FEATURE:
<223> OTHER INFORMATION: primer

<400> SEQUENCE: 27
ccccagcgac cctgatta                                                   18

<210> SEQ ID NO 28
<211> LENGTH: 21
<212> TYPE: DNA
<213> ORGANISM: Artificial Sequence
<220> FEATURE:
<223> OTHER INFORMATION: primer

<400> SEQUENCE: 28
ggacacaaac tcaaatggtg g                                               21

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
attcgttggg gatgacagag                                                 20
```

```
<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
tgggatccag aggcttattg                                              20

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
agcagtgcaa gagtccctgt                                              20

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
cacagcctct acctcggaac                                              20
```

ENDODERMAL CELL PRODUCTION METHOD, LIVER CELL PRODUCTION METHOD, PANCREATIC CELL PRODUCTION METHOD, ENDODERMAL CELL INDUCTION PROMOTER, LIVER CELL INDUCTION PROMOTING KIT, PANCREATIC CELL INDUCTION PROMOTING KIT, AND MICROFLUIDIC DEVICE

TECHNICAL FIELD

The present invention relates to an endodermal cell production method, a liver cell production method, a pancreatic cell production method, an endodermal cell induction promoter, a liver cell induction promoting kit, a pancreatic cell induction promoting kit, and a microfluidic device.

BACKGROUND ART

For evaluation of drug functions etc., attempts have been made to differentiate pluripotent cells such as embryonic stem cells (ES cells) or induced pluripotent stem cells (iPS cells) into hepatocyte-like cells (also referred to as "liver cells" hereinafter). A known method for inducing differentiation of the pluripotent cells into the liver cells is transferring a gene involved in liver cell differentiation into the pluripotent cells. Non-Patent Document 1 discloses a method for inducing differentiation of pluripotent cells forming cell clusters into liver cells.

However, the gene transfer has a risk of cancerous transformation of the cells to which the gene has been transferred, for example. Also, the method disclosed in Non-Patent Document 1 has problems in that: most of the cells die at an early stage of differentiation; and it is difficult to produce uniform cell clusters suitable for the liver cell induction.

CITATION LIST

Non-Patent Document(s)

Non-Patent Document 1: Hannan, N. R. F. et at, "Production of hepatocyte like cells from human pluripotent stem cells", Nature Protocols, volume 8, number 2, pages 430-437

BRIEF SUMMARY OF THE INVENTION

Problem to be Solved by the Invention

With the foregoing in mind, it is an object of the present invention to provide an endodermal cell production method that can induce differentiation of pluripotent cells into endodermal cells even when the pluripotent cells are dispersed, and can achieve improved endodermal cell production efficiency.

Means for Solving Problem

In order to achieve the above object, the present invention provides a method for producing endodermal cells by inducing differentiation of pluripotent cells into the endodermal cells, including the step of: inducing differentiation of the pluripotent cells into the endodermal cells in the presence of an endodermal cell inducing factor, wherein, in the induction step, ROCK protein activity is inhibited.

The present invention also provides a liver cell production method including the step of: differentiating endodermal cells into liver cells in the presence of a liver cell differentiation factor, wherein the endodermal cells are obtained by the endodermal cell production method according to the present invention.

The present invention also provides a pancreatic cell production method including the step of: differentiating endodermal cells into pancreatic cells in the presence of a pancreatic cell differentiation factor, wherein the endodermal cells are obtained by the endodermal cell production method according to the present invention.

The present invention also provides an endodermal cell induction promoter containing: a ROCK protein activity inhibitor.

The present invention also provides a liver cell induction promoting kit including: the endodermal cell induction promoter according to the present invention.

The present invention also provides a pancreatic cell induction promoting kit including: the endodermal cell induction promoter according to the present invention.

The present invention also provides a microfluidic device for use in the liver cell production method of the present invention. The microfluidic device includes: at least two openings; and a cell culture chamber, the openings communicating with the cell culture chamber, wherein, during culture of liver cells on a scaffold to be carried out after introducing the liver cells and the scaffold into the cell culture chamber, a liver cell maturation factor can be supplied to the cell culture chamber through at least one of the openings while forming a concentration gradient in the cell culture chamber.

Effects of the Invention

The endodermal cell production method according to the present invention can induce differentiation of pluripotent cells into endodermal cells even when the pluripotent cells are dispersed and can achieve improved endodermal cell production efficiency.

MODE FOR CARRYING OUT THE INVENTION

Figure 1A:
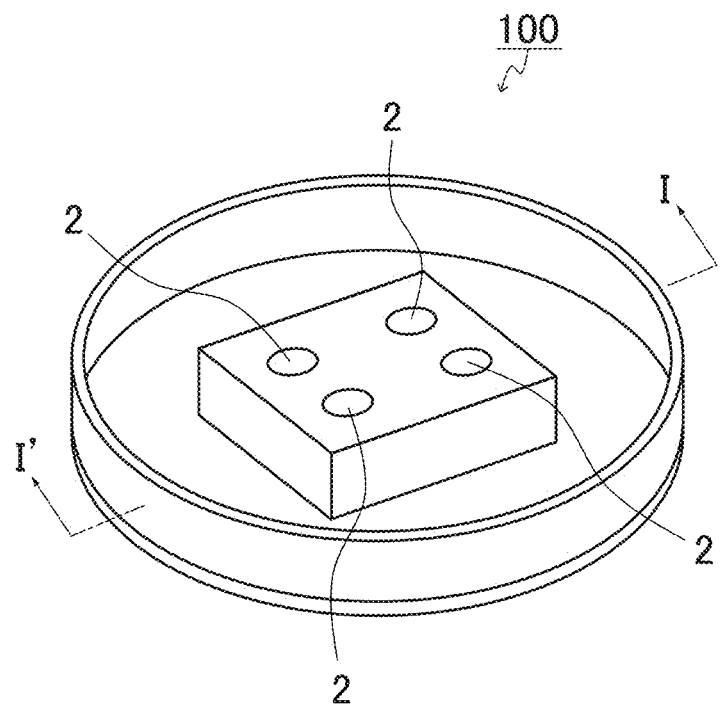
FIG. 1A is a perspective view showing the configuration a device according to an embodiment.

In the endodermal cell production method of the present invention, it is preferable that, in the induction step, a cell density of the pluripotent cells at the start of the induction is from $0.5 \times 10^4$ to $2 \times 10^5$ cells/cm$^2$.

In the endodermal cell production method of the present invention, it is preferable that the pluripotent cells are dispersed.

In the endodermal cell production method of the present invention, the endodermal cell inducing factor includes, for example, at least one selected from the group consisting of a TGF-β family protein, bFGF, a PI$_3$K protein activity inhibitor, a GSK-3β protein activity inhibitor, and an mTOR protein activity inhibitor. Preferably, the TGF-β family protein includes at least one selected from the group consisting of activin, BMP-4, and NODAL.

In the endodermal cell production method of the present invention, the induction step is, for example, a step of inducing differentiation of the pluripotent cells into the endodermal cells in the presence of a pluripotent cell culture solution containing the endodermal cell inducing factor. Preferably, the pluripotent cell culture solution contains a TGF-β family protein(s) and bFGF. More preferably, the pluripotent cell culture solution contains a TGF-β family protein(s), bFGF, and insulin.

In the endodermal cell production method of the present invention, it is preferable that, in the induction step, the ROCK protein activity is inhibited by a ROCK protein activity inhibitory compound, for example.

In the liver cell production method of the present invention, the liver cell differentiation factor includes, for example, at least one selected from the group consisting of a TGF-β family protein, FGF10, and WNT. Preferably, the TGF-β family protein includes at least one selected from the group consisting of activin, BMP-4, and NODAL.

The liver cell production method of the present invention may further include the step of: maturing the liver cells in the presence of a liver cell maturation factor, for example.

In the liver cell production method of the present invention, it is preferable that, in the maturation step, the liver cells are matured on a scaffold. It is more preferable that the scaffold is at least one selected from the group consisting of a coating containing an extracellular matrix protein(s), a coating containing a blood component(s), and a coating containing a recombinant protein(s). It is still more preferable that the scaffold is a coating containing an extracellular matrix protein(s).

In the liver cell production method of the present invention, the liver cell maturation factor includes, for example, at least one selected from the group consisting of OSM, HGF, dexamethasone, nicotinamide, dimethyl sulfoxide, and sodium butyrate.

In the liver cell production method of the present invention, it is preferable that, in the maturation step, the liver cells are matured in a microfluidic device (also referred to simply as "device" hereinafter). The microfluidic device includes: at least two openings; and a cell culture chamber. The openings communicate with the cell culture chamber, and during culture of liver cells on a scaffold to be carried out after introducing the liver cells and the scaffold into the cell culture chamber, the liver cell maturation factor can be supplied to the cell culture chamber through at least one of the openings while forming a concentration gradient in the cell culture chamber. It is more preferable that, in the maturation step, the cell density of the liver cells at the start of the maturation is from $1 \times 10^4$ to $5 \times 10^4$ cells/cm$^2$.

In the endodermal cell induction promoter of the present invention, the substance that inhibits the ROCK protein activity is, for example, a ROCK protein activity inhibitory compound.

The endodermal cell induction promoter of the present invention may further contain an endodermal cell inducing factor, for example. The endodermal cell inducing factor includes at least one selected from the group consisting of a TGF-β family protein, bFGF, a PI$_3$K protein activity inhibitor, a GSK-3β protein activity inhibitor, and an mTOR protein activity inhibitor. Preferably, the TGF-β family protein includes at least one selected from the group consisting of activin, BMP-4, and NODAL.

The liver cell induction promoting kit of the present invention may further include a liver cell differentiation factor, for example. The liver cell differentiation factor includes at least one selected from the group consisting of TGF-β family proteins, FGF10, and WNT. Preferably, the TGF-β family protein includes at least one selected from the group consisting of activin, BMP-4, and NODAL.

The liver cell induction promoting kit of the present invention may further include a liver cell maturation factor, for example. The liver cell maturation factor includes at least one selected from the group consisting of OSM, HGF, dexamethasone, nicotinamide, dimethyl sulfoxide, and sodium butyrate.

The liver cell induction promoting kit of the present invention preferably is configured so that it further includes a microfluidic device including: at least two openings; and a cell culture chamber, the openings communicating with the cell culture chamber, wherein, during culture of liver cells on a scaffold to be carried out after introducing the liver cells and the scaffold into the cell culture chamber, the liver cell maturation factor can be supplied to the cell culture chamber through at least one of the openings while forming a concentration gradient in the cell culture chamber.

In the pancreatic cell production method and the pancreatic cell induction promoting kit according to the present invention, the pancreatic cell differentiation factor is, for example, at least one selected from the group consisting of KGF, EGF, FGF2, FGF7, FGF10, hedgehog signal inhibitors, retinoic acid receptor activators, Noggin, and ALK inhibitors.

In the present invention, the term "ROCK protein" means Rho-associated coiled-coil forming kinase.

In the present invention, the term "pluripotent" means, for example, being capable of differentiating into the three germ layers including endoderm, mesoderm, and ectoderm. Also, in the present invention, the term "pluripotent" encompasses, for example, being capable of differentiating into all types of cells, i.e., being totipotent.

In the present invention, "inhibition of the activity of a protein" means, for example, inhibiting the activity of a protein. The mechanism of the inhibition is not particularly limited, and may be, for example, inhibition of the activity of the protein itself, or may be inhibition of the expression of the protein. In the latter case, inhibition of the expression may be downregulation or silencing, for example. Whether the expression of the protein has been inhibited can be determined by, for example, a decrease in the amount of a transcription product of a target gene, a decrease in the activity of the transcription product, a decrease in the amount of a translation product of the target gene, or a decrease in the activity of the translation product.

<Endodermal Cell Production Method>

The endodermal cell production method according to the present invention is, as described above, a method for producing endodermal cells by inducing differentiation of pluripotent cells into the endodermal cells, including the step of: inducing differentiation of the pluripotent cells into the endodermal cells in the presence of an endodermal cell inducing factor, wherein, in the induction step, ROCK protein (also referred to simply as "ROCK" hereinafter) activity is inhibited. The endodermal cell production method of the present invention is characterized in that the ROCK protein activity is inhibited in the induction step, and other steps or conditions are not particularly limited.

The inventors of the present invention have found out through diligent research that, in induction of differentiation of pluripotent cells into endodermal cells, it is possible to inhibit cell death during the induction and to promote cell proliferation by inhibiting the ROCK activity, for example. Thus, the endodermal cell production method of the present invention can improve the efficiency of endodermal cell production. Inhibiting the ROCK activity when inducing differentiation of pluripotent cells into other cells is a novel approach that is not used in the method disclosed in the above-described prior art document, for example, and this approach was adopted first by the inventors of the present invention. The inventors of the present invention also have found out through diligent research that, by inhibiting the ROCK activity, it is possible to induce differentiation of pluripotent cells into endodermal cells even when the pluripotent cells are dispersed, thereby achieving the present invention. According to the present invention that can induce differentiation of the dispersed pluripotent cells into endodermal cells, it is not necessary to use pluripotent cells forming cell clusters for endodermal cell induction as in the prior art document. Thus, the present invention eliminates the necessity of forming uniform pluripotent cell clusters, so that differentiation into endodermal cells can be induced with simpler procedures, for example. Furthermore, the inventors of the present invention also found out that, by using endodermal cells obtained by the endodermal cell production method of the present invention, the number of days required for induction and maturation of liver cells and pancreatic cells can be shortened as compared with the number of days required in the method disclosed in the prior art document, for example, although the mechanism thereof is not clear. Therefore, according to the endodermal cell production method of the present invention, endodermal cells that can differentiate into mature liver cells and pancreatic cells in a shorter period can be produced, for example.

The pluripotent cells are not particularly limited, and examples thereof include ES cells, iPS cells, nuclear transfer ES cells (ntES cells), germinal stem cells, somatic stem cells, and embryonal carcinoma cells. The source of the pluripotent cells is not particularly limited, and examples thereof include humans and non-human animals excluding humans. Examples of the non-human animals include primates such as monkeys, gorillas, chimpanzees, and marmosets, mice, rats, dogs, rabbits, sheep, horses, and guinea pigs.

The endodermal cell inducing factor may be, for example, a TGF-β family protein, a basic fibroblast growth factor (bFGF), a PI$_3$K protein (also referred to simply as "PI$_3$K" hereinafter) activity inhibitor, a a GSK-3β protein (also referred to simply as "GSK-3β" hereinafter) activity inhibitor, or an mTOR protein (also referred to simply as "mTOR" hereinafter) activity inhibitor. The TGF-β family protein is not particularly limited, and examples thereof include activin A, bone morphogenetic protein 4 (BMP-4), and NODAL. The PI$_3$K activity inhibitor is not particularly limited, and may be a PI$_3$K activity inhibitory compound or a PI$_3$K activity inhibitory nucleic acid, for example. In the former case, the PI$_3$K activity inhibitory compound may be, for example, a known PI$_3$K activity inhibitory compound, such as, e.g., LY294002, Wortmannin, PI828, TG100713, or PF05212384. In the latter case, the PI$_3$K activity inhibitory nucleic acid may be, for example, an expression inhibitory nucleic acid such as siRNA or miRNA that targets mRNA encoding PI$_3$K. The GSK-3β activity inhibitor is not particularly limited, and may be a GSK-3β activity inhibitory compound or a GSK-3β activity inhibitory nucleic acid, for example. In the former case, the GSK-3β activity inhibitory compound may be, for example, a known GSK-3β activity inhibitory compound, such as CHIR99021, BIO, MeBIO, SB216763, TWS119, 3F8, or TC-G24. In the latter case, the GSK-3β activity inhibitory nucleic acid may be, for example, an expression inhibitory nucleic acid such as siRNA or miRNA that targets mRNA encoding GSK-3β. The mTOR activity inhibitor is not particularly limited, and may be an mTOR activity inhibitory compound or an mTOR activity inhibitory nucleic acid, for example. In the former case, the mTOR activity inhibitory compound may be, for example, a known mTOR activity inhibitory compound, such as Rapamycin, KU0063794, PP242, Torin1, Torin2, WYE687 dihydrochloride, or XL388. In the latter case, the mTOR activity inhibitory nucleic acid may be, for example, an expression inhibitory nucleic acid such as siRNA or miRNA that targets mRNA encoding mTOR. When the endodermal cell inducing factor is a protein, the source of the endodermal cell inducing factor may be the same as or different from the source of the pluripotent cells. One type of endodermal cell inducing factor may be used alone, or two or more types of endodermal cell inducing factors may be used in combination, for example. In the latter case, the combination of the endodermal cell inducing factors is not particularly limited, and examples thereof include: the combination of activin A, BMP-4, and the PI$_3$K activity inhibitor; the combination of activin A, BMP-4, the PI$_3$K activity inhibitor, and the GSK-3β activity inhibitor; and the combination of activin A and the GSK-3β activity inhibitor. In the induction of differentiation of the pluripotent cells into the endoderm cells, the same endodermal cell inducing factor may be used over the entire period, or different endodermal cell inducing factors may be used for respective predetermined periods. As to the predetermined periods, reference can be made to Examples etc. to be described below, for example.

The endodermal cells are not particularly limited, and may be cells capable of differentiating into cells derived from endoderm. Examples of the endoderm-derived cells include digestive system cells, liver cells, and pancreatic cells. The endodermal cells may be calls capable of differentiating into one type of endoderm-derived cells or cells capable of differentiating into two or more types of endoderm-derived cells, for example. The endodermal cells can be identified by the expression of an endodermal cell marker(s), for example. Examples of the endodermal cell marker include SOX17, CXCR4, hepatocyte nuclear factor-3β (HNF-3β, FoxA2), and goosecoid (GSC). Human-derived SOX17 has, as cDNA, the base sequence registered under NCBI Accession No. NM_022454, for example. Human-derived CXCR4 has, as cDNA, the base sequence registered under NCBI Accession No. NM_003467, for example. Human-derived HNF-3β has, as cDNA, the base sequence registered under NCBI Accession No. NM_021784 or NM_153675, for example. Human-derived GSC has, as cDNA, the base sequence registered under NCBI Accession No. NM_173849, for example. In the endodermal cell production method of the present invention, cells expressing one type of endodermal cell marker may be identified as the endodermal cells, or cells expressing two or more types of endodermal cell markers may be identified as the endodermal cells, for example. Preferably, cells expressing all the endodermal cell markers are identified as the endodermal cells, because such endodermal cells have properties closer to those of endodermal cells in vivo.

In the induction step, the differentiation of the pluripotent cells into the endodermal cells can be induced by culturing the pluripotent cells in the presence of a culture solution (also referred to as "induction culture solution" hereinafter), for example. When the differentiation of the pluripotent cells is induced in the presence of the induction culture solution, the induction culture solution contains the endodermal cell inducing factor, for example. The induction culture solution is not particularly limited, and may be a pluripotent cell culture solution, RPMI1640, DMEM, DMEM/F12, Iscove (IMEM), or αMEM, for example. Examples of the pluripotent cell culture solution include mTeSR-1 (STEMCELL Technologies), TeSR-E8 (STEMCELL Technologies), CDM-PVA, StemPRO hESC SFM (Life Technologies), and E8 (Life Technologies). Among them, mTeSR-1, TeSR-E8, and E8 are preferable. As to the composition of CDM-PVA, reference can be made to Non-Patent Document 1, for example. The induction culture solution preferably is a culture solution containing a TGF-β family protein and bFGF, more preferably a culture solution containing a TGF-β family protein, bFGF, and insulin, from the viewpoint of further improving the efficiency of differentiation into the endodermal cells, for example. Specific examples of an induction culture solution containing two or three types of these factors include mTeSR-1 and E8. In the induction of the differentiation of the pluripotent cells into the endoderm cells, the same induction culture solution may be used over the entire period, or different induction culture solutions may be used for respective predetermined periods. As to the predetermined periods, reference can be made to Examples etc. to be described below, for example.

The induction culture solution also may contain other components. The other components are not particularly limited, and examples thereof include culture supplements, serum, and antibiotics. Examples of the culture supplements include GlutaMAX™ supplements (GIBCO), B-27® supplements, and non-essential amino acid (NEAA) supplements. Examples of the antibiotics include penicillin and streptomycin.

In the induction step, the differentiation of the pluripotent cells into the endodermal cells may be induced using feeder cells or without using feeder cells, for example. As the feeder cells, known feeder cells such as mouse embryonic fibroblasts can be used, for example. When the differentiation is induced without using the feeder cells, it is preferable to mature the pluripotent cells on a scaffold. The scaffold is not particularly limited, and may be, for example, an extracellular matrix protein-containing coating, a blood component-containing coating, a coating agent-containing coating, or a recombinant protein-containing coating. Among them, the extracellular matrix protein-containing coating is preferable. Examples of the extracellular matrix protein include: laminins such as laminin 111; collagens such as type I collagen and type IV collagen; entactin; and heparan sulfate proteoglycans. The extracellular matrix protein-containing coating may contain one type of extracellular matrix protein, or two or more types of extracellular matrix proteins The extracellular matrix protein-containing coating is, for example, a coating containing Matrigel™ (BD Biosciences), a coating containing a collagen(s), or a coating containing a laminin(s). The blood component-containing coating is not particularly limited, and is, for example, a coating formed of a blood specimen such as whole blood, serum, or plasma, or a hemoprotein such as fibronectin. The coating agent is, for example, Synthemax® (Corning). Examples of the recombinant protein include modified proteins, fusion proteins, and the like of the above-described extracellular matrix proteins. The scaffold can be produced by incubating the serum, the extracellular matrix protein, or the like in a culture vessel, for example. One type of scaffold may be used alone, or two or more types of scaffolds may be used in combination, for example.

In the induction step, the cell density of the pluripotent cells at the start of the induction corresponds to the cell density of the pluripotent cells when they were seeded in the culture vessel, for example. Thus, it also can be referred to as the seeding density of the pluripotent cells. The cell density of the pluripotent cells at the start of the induction is not particularly limited, and is, for example, from $0.5 \times 10^4$ to $2 \times 10^5$ cells/cm$^2$. The cell density preferably is from $1 \times 10^4$ to $7 \times 10^4$ cells/cm$^2$, more preferably from $2 \times 10^4$ to $6 \times 10^4$ cells/cm$^2$, from the viewpoint of further improving the efficiency of differentiation into the endodermal cells. The pluripotent cells at the start of the induction may be dispersed or may form cell clusters, for example. Preferably, the pluripotent cells at the start of the induction are dispersed, from the viewpoint of further improving the efficiency of differentiation into the endodermal cells. The dispersed pluripotent cells can be obtained by treating the pluripotent cells forming cell clusters with protease, for example. The conditions of the protease treatment are not particularly limited, and may be conditions commonly used for cell separation, for example. The protease is not particularly limited, and may be a known protease used in cell culture and the like, for example. Specific examples of the protease include: trypsin; trypsin derivatives such as TrypLE™ express (Life Technologies); Accutase; collagenase; and Dispase. The protease treatment may be performed in the presence of a known calcium chelating agent such as EDTA, for example. When the pluripotent cells forming cell clusters are used, the cell density of the pluripotent cells at the start of the induction is, for example, from $1 \times 10^4$ to $2 \times 10^5$ cells/cm$^2$. The cell density preferably is from $2.5 \times 10^4$ to $2 \times 10^5$ cells/cm$^2$, more preferably from $5 \times 10^4$ to $1 \times 10^5$ cells/cm$^2$, from the viewpoint of further improving the efficiency of differentiation into the endodermal cells. When the dispersed pluripotent cells are used, the cell density of the pluripotent cells at the start of the induction is, for example, from $0.5\times10^4$ to $2\times10^5$ cells/cm². The cell density preferably is from $1\times10^4$ to $7\times10^4$ cells/cm², more preferably from $2\times10^4$ to $6\times10^4$ cells/cm², from the viewpoint of further improving the efficiency of differentiation into the endodermal cells. The cell density can be calculated from the growth area of the culture vessel used for the induction and the number of the cells, for example.

In the induction step, the number of days for which the differentiation of the pluripotent cells into the endodermal cells is induced (also referred to as "induction period" hereinafter) is not particularly limited, and is, for example, from 3 to 8 days, preferably from 4 to 5 days.

In the induction step, the method for inhibiting the ROCK activity is not particularly limited, and examples thereof include using a ROCK activity inhibitor. When the ROCK activity inhibitor is used, the differentiation of the pluripotent cells into the endodermal cells can be induced by culturing the pluripotent cells in the presence of the ROCK activity inhibitor, for example. The ROCK activity inhibitor is not particularly limited, and may be a ROCK activity inhibitory compound or ROCK activity inhibitory nucleic acid, for example. In the former case, the ROCK activity inhibitory compound may be, for example, a known ROCK activity inhibitory compound such as Y27632 or Fasudil (HA1077). In the latter case, the ROCK activity inhibitory nucleic acid may be, for example, an expression inhibitory nucleic acid such as siRNA or miRNA that targets mRNA encoding the ROCK. One type of ROCK activity inhibitor may be used alone, or two or more types of ROCK activity inhibitors may be used in combination. When the ROCK activity inhibitor is used, the concentration of the ROCK activity inhibitor is not particularly limited, and may be, for example, from $1\times10^{-6}$ to $1\times10^{-4}$ mol/l, preferably from $2\times10^{-6}$ to $2\times10^{-5}$ mol/l. The concentration of the ROCK activity inhibitor may be, for example, the concentration of one type of ROCK activity inhibitor or the sum of the concentrations of two or more types of ROCK activity inhibitors (the same applies hereinafter). The ROCK activity inhibitory compound may control the activity of myosin whose polymerization and depolymerization is controlled by ROCK, or may control the activity of a protein that activates ROCK, for example. In the former case, the ROCK activity inhibitory compound may be a myosin depolymerizing agent, for example. The myosin depolymerizing agent may be, for example, a known myosin depolymerizing agent such as Blebbistatin.

In the induction step, the number of days for which the ROCK activity is inhibited is not particularly limited. For example, the ROCK activity may be inhibited during the entire induction period or part of the induction period. In the latter case, the start date and the end date of the inhibition of the ROCK activity in the induction period are not particularly limited. In the induction step, the efficiency of differentiation into the endodermal cells can be improved by inhibiting the ROCK activity in an early stage of the induction of differentiation into the endodermal cells, for example. On this account, the start date of the inhibition of the ROCK activity preferably is the start date of the induction period. The end date is not particularly limited, and may be, for example, the day on which the pluripotent cells undergoing the induction acquire the adhesiveness to the culture vessel. In the induction period, the number of days for which the ROCK activity is inhibited is not particularly limited. For example, the ratio (S:I) between the number of days for which the ROCK activity is inhibited (S) and the number of days in the induction period (I) is 1:2 to 7, 1:2 to 6, or 1:3 to 4. Specifically, the number of days for which the ROCK activity is inhibited is from 1 to 7 days, from 2 to 6 days, or from 3 to 4 days, for example.

In the induction step, the concentration of the endodermal cell inducing factor is not particularly limited, and may be from $1\times10^{-12}$ to $1\times10^{-6}$ mol/l, for example. The concentration of the endodermal cell inducing factor may be, for example, the concentration of one type of endodermal cell inducing factor or the sum of the concentrations of two or more types of endodermal cell inducing factors (the same applies hereinafter). When the endodermal cell inducing factor contains a TGF-β family protein, the concentration of the TGF-β family protein is from $1\times10^{-10}$ to $1\times10^{-7}$ mol/l or $1\times10^{-9}$ to $5\times10^{-9}$ mol/l, for example. When the endodermal cell inducing factor contains activin A, the concentration of the activin A is from $1\times10^{-10}$ to $1\times10^{-7}$ mol/l or $1\times10^{-9}$ to $5\times10^{-9}$ mol/l, for example. When the endodermal cell inducing factor contains BMP-4, the concentration of the BMP-4 is from $1\times10^{-11}$ to $1\times10^{-9}$ mol/l or $1\times10^{-10}$ to $5\times10^{-10}$ mol/l, for example. When the endodermal cell inducing factor contains bFGF, the concentration of the bFGF is from $1\times10^{-10}$ to $1\times10^{-7}$ mol/l or $1\times10^{-9}$ to $5\times10^{-9}$ mol/l, for example. When the endodermal cell inducing factor contain a PI$_3$K protein activity inhibitor, the concentration of the substance is from $1\times10^{-6}$ to $1\times10^{-4}$ mol/l or $5\times10^{-6}$ to $2\times10^{-5}$ mol/l, for example. When the endodermal cell inducing factor contains a substance that inhibits the activity of GSK-3β, the concentration of the substance is from $1\times10^{-6}$ to $1\times10^{-4}$ mol/l or $1\times10^{-6}$ to $5\times10^{-6}$ mol/l, for example.

The combination of the cell density of the pluripotent cells at the start of the induction, the concentration of the ROCK activity inhibitor, and the concentration of the endodermal cell inducing factor is not particularly limited. When the cell density of the pluripotent cells at the start of the induction is from $0.5\times10^4$ to $2\times10^5$ cells/cm², the concentration of the ROCK activity inhibitor is from $1\times10^{-6}$ to $1\times10^{-4}$ mol/l and the concentration of the endodermal cell inducing factor is from $1\times10^{-12}$ to $1\times10^{-6}$ mol/l, for example. Although the combination of the three components is shown above, only two out of the three components may be used in combination.

In the induction step, the culture conditions are not particularly limited, and culture conditions commonly used for pluripotent cells may be used, for example. In the induction step, the O$_2$ partial pressure is, e.g., from 1% to 21%, and the CO$_2$ partial pressure is, e.g., from 5% to 6%. The culture temperature is from 36° C. to 37° C., for example.

The induction step will be described below with reference to an example where activin A, BMP-4, bFGF, a PI$_3$K activity inhibitory compound, and a GSK-3β activity inhibitory compound are used as the endodermal cell inducing factors, and the ROCK activity is inhibited by a ROCK activity inhibitory compound. It is to be noted, however, that this example is merely illustrative and does not limit the present invention by any means.

First, pluripotent cells suspended in a first culture solution are seeded in a culture vessel. The cell density of the pluripotent cells at the start of the induction is from $0.5\times10^4$ to $2\times10^5$ cells/cm², for example. The first culture solution is an induction culture solution containing $1\times10^{-10}$ to $1\times10^{-7}$ mol/l activin A and $1\times10^{-6}$ to $1\times10^{-4}$ mol/l ROCK activity inhibitory compound, for example. The culture conditions are not particularly limited, and the O$_2$ partial pressure is, e.g., from 1% to 21%, and the CO$_2$ partial pressure is, e.g., from 5% to 6%. The culture temperature is from 36° C. to 37° C., for example. Under the above-described culture conditions, the cells are cultured for 12 to 48 hours, for example.

Next, the first culture solution is removed, and a second culture solution is added. The second culture solution is an induction culture solution containing $1\times10^{-10}$ to $1\times10^{-7}$ mol/l activin A, $1\times10^{-11}$ to $1\times10^{-9}$ mol/l BMP-4, $1\times10^{-6}$ to $1\times10^{-4}$ mol/l PI$_3$K activity inhibitory compound, $1\times10^{-6}$ to $1\times10^{-4}$ mol/l GSK-3β activity inhibitory compound, and $1\times10^{-6}$ to $1\times10^{-4}$ mol/l ROCK activity inhibitory compound, for example. Under the above-described culture conditions, the cells are cultured for 12 to 36 hours, for example.

Next, the second culture solution is removed, and a third culture solution is added. The third culture solution is an induction culture solution containing $1\times10^{-10}$ to $1\times10^{-7}$ mol/l activin A, $1\times10^{-11}$ to $1\times10^{-9}$ mol/l BMP-4, $1\times10^{-6}$ to $1\times10^{-4}$ mol/l PI$_3$K activity inhibitory compound, and $1\times10^{-6}$ to $1\times10^{-4}$ mol/l ROCK activity inhibitory compound, for example. Under the above culture conditions, the cells are cultured for 12 to 36 hours, for example.

Then, by collecting the cultured cells, endodermal cells can be obtained. The induction step may further include cell culture using a fourth culture solution to be described below.

When the induction step includes cell culture using the fourth culture solution, the third culture solution is removed, and the fourth culture solution is added. The fourth culture solution is an induction culture solution containing $1\times10^{-10}$ to $1\times10^{-7}$ mol/l activin A and $1\times10^{-10}$ to $1\times10^{-7}$ mol/l bFGF, for example. Under the above-described culture conditions, the cells are cultured for 12 to 36 hours, for example.

Then, by collecting the cultured cells, endodermal cells can be obtained.

<Liver Cell Production Method>

The liver cell production method according to the present invention is, as described above, a liver cell production method including the step of: differentiating endodermal cells into liver cells in the presence of a liver cell differentiation factor, wherein the endodermal cells are obtained by the endodermal cell production method according to the present invention. The liver cell production method of the present invention is characterized in that the endodermal cells are obtained by the endodermal cell production method of the present invention, and other steps or conditions are not particularly limited. The liver cell production method of the present invention can induce differentiation of pluripotent cells into endodermal cells even when the pluripotent cells are dispersed and can achieve improved endodermal cell production efficiency. The above description regarding the endodermal cell production method of the present invention also applies to the liver cell production method of the present invention, for example.

The liver cell production method of the present invention may include, prior to the differentiation step, an induction step of inducing differentiation into endodermal cells by the endodermal cell production method of the present invention. The induction step can be carried out in the same manner as the induction step in the endodermal cell production method of the present invention, for example.

The liver cell differentiation factor may be a TGF-β family protein, fibroblast growth factor 10 (FGF10), or WNT, for example. The TGF-β family protein is not particularly limited, and examples thereof include activin A, BMP-4, and NODAL. When the liver cell differentiation factor is a protein, the source of the liver cell differentiation factor may be the same as or different from the source of the endodermal cells, i.e., the source of the above-described pluripotent cells. One type of liver cell differentiation factor may be used alone, or two or more types of liver cell differentiation factors may be used in combination, for example. In the latter case, the combination of the liver cell differentiation factors is not particularly limited, and examples thereof include; the combination of BMP-4 and FGF10; and the combination of BMP-4 and WNT. In the differentiation of the endodermal cells into the liver cells, the same liver cell differentiation factor may be used over the entire period, or different liver cell differentiation factors may be used for respective predetermined periods. As to the predetermined periods, reference can be made to Examples etc. to be described below, for example.

The liver cells can be identified by the expression of a liver cell marker(s), for example. Examples of the liver cell marker include α-fetoprotein (AFP), hepatocyte nuclear factor 4 alpha (HNF4α), tyrosine aminotransferase (TAT), transthyretin (TTR), apolipoprotein F (ApoF), constitutive androstane receptor (CAR), and tryptophan 2,3-dioxygenase (TDO2, TO). Human-derived AFP has, as cDNA, the base sequence registered under NCBI Accession No. NM_001134, for example. Human-derived HNF4α has, as cDNA, the base sequence registered under NCBI Accession No. NM_000457, for example. Human-derived TAT has, as cDNA, the base sequence registered under NCBI Accession No. NM_000353, for example. Human-derived TTR has, as cDNA, the base sequence registered under NCBI Accession No. NM_000371, for example. Human-derived ApoF has, as cDNA, the base sequence registered under NCBI Accession No. NM_001638, for example. Human-derived CAR has, as cDNA, the base sequence registered under NCBI Accession No. NM_001077469, for example. Human-derived TDO2 has, as cDNA, the base sequence registered under NCBI Accession No. NM_005651, for example. In the liver cell production method of the present invention, cells expressing one type of liver cell marker may be identified as the liver cells, or cells expressing two or more types of liver cell markers may be identified as the liver cells, for example. Preferably, cells expressing all the liver cell markers are identified as the liver cells, because such liver cells have properties closer to those of liver cells in vivo.

In the differentiation step, the differentiation of the endodermal cells into the liver cells can be performed by culturing the endodermal cells in the presence of a culture solution (also referred to as "differentiation culture solution" hereinafter), for example. When the differentiation into the liver cells is performed in the presence of the differentiation culture solution, the differentiation culture solution contains the liver cell differentiation factor, for example. The differentiation culture solution is not particularly limited, and may be an RPMI1640 medium, DMEM, DMEM/F12, Iscove (IMEM), or αMEM, for example. In the differentiation of the endodermal cells into the liver cells, the same differentiation culture solution may be used over the entire period, or different differentiation culture solutions may be used for respective predetermined periods. As to the predetermined periods, reference can be made to Examples etc. to be described below, for example.

The differentiation culture solution also may contain other components. As to the other components, reference can be made to the above description regarding the other components, for example.

In the differentiation step, the differentiation of the endodermal cells into the liver cells may be performed using feeder cells or without using feeder cells, for example. As to the feeder cells, reference can be made to the above description regarding the feeder cells, for example. When the differentiation is performed without using the feeder cells, it is preferable to mature the endodermal cells on a scaffold. As to the scaffold, reference can be made to the above description regarding the scaffold, for example.

In the differentiation step, the endodermal cells are not limited as long as they are endodermal cells obtained by the endodermal cell production method of the present invention. When the liver cell production method of the present invention includes the induction step, the endodermal cells obtained in the induction step may be used as they are, or the endodermal cells obtained in the induction step may be collected and the collected endodermal cells may be seeded, for example. When the endodermal cells are seeded, the cell density of the endodermal cells at the start of the differentiation is not particularly limited, and may be, for example, from $1 \times 10^4$ to $2 \times 10^5$ cells/cm$^2$. The cell density preferably is from $2.5 \times 10^4$ to $2 \times 10^5$ cells/cm$^2$, more preferably from $5 \times 10^4$ to $1 \times 10^5$ cells/cm$^2$, from the viewpoint of further improving the efficiency of differentiation into the liver cells. The cell density can be calculated from the growth area of the culture vessel used for the differentiation and the number of the cells, for example.

In the differentiation step, the number of days for which the differentiation of the endodermal cells into the liver cells is performed (also referred to as "differentiation period" hereinafter) is not particularly limited, and is, for example, from 3 to 14 days, preferably from 5 to 8 days.

In the differentiation step, the concentration of the liver cell differentiation factor is not particularly limited, and may be from $1 \times 10^{-12}$ to $1 \times 10^{-6}$ mol/l, for example. The concentration of the liver cell differentiation factor may be, for example, the concentration of one type of liver cell differentiation factor or the sum of the concentrations of two or more types of liver cell differentiation factors (the same applies hereinafter). When the liver cell differentiation factor contains a TGF-β family protein, the concentration of the TGF-β family protein is from $1 \times 10^{-10}$ to $1 \times 10^{-7}$ mol/l or $1 \times 10^{-9}$ to $5 \times 10^{-9}$ mol/l, for example. When the liver cell differentiation factor contains activin A, the concentration of the activin A is from $1 \times 10^{-10}$ to $1 \times 10^{-7}$ mol/l or $1 \times 10^{-9}$ to $5 \times 10^{-9}$ mol/l, for example. When the liver cell differentiation factor contains BMP-4, the concentration of the BMP-4 is from $1 \times 10^{-11}$ to $1 \times 10^{-9}$ mol/l or $1 \times 10^{-10}$ to $5 \times 10^{-10}$ mol/l, for example. When the liver cell differentiation factor contains FGF10, the concentration of the FGF10 is from $1 \times 10^{-13}$ to $1 \times 10^{-11}$ mol/l or $1 \times 10^{-12}$ to $1 \times 10^{-11}$ mol/l, for example. When the liver cell differentiation factor contains WNT, the concentration of the WNT is from $1 \times 10^{-14}$ to $1 \times 10^{-11}$ mol/l or $2 \times 10^{-13}$ to $1 \times 10^{-12}$ mol/l, for example.

When the liver cell production method of the present invention includes the induction step, the combination of the cell density of the pluripotent cells at the start of the induction and the concentration of the liver cell differentiation factor is not particularly limited. When the cell density of the pluripotent cells at the start of the induction is from $0.5 \times 10^4$ to $2 \times 10^5$ cells/cm$^2$, the concentration of the liver cell differentiation factor is from $1 \times 10^{-12}$ to $1 \times 10^{-6}$ mol/l, for example.

The combination of the cell density of the endodermal cells at the start of the differentiation and the concentration of the liver cell differentiation factor is not particularly limited. When the cell density of the endodermal cells at the start of the differentiation is from $1 \times 10^4$ to $2 \times 10^5$ cells/cm$^2$, the concentration of the liver cell differentiation factor is from $10^{-12}$ to $1 \times 10^{-6}$ mol/l, for example.

In the differentiation step, the culture conditions are not particularly limited, and the above description regarding the culture conditions in the induction step also applies to the culture conditions in the differentiation step, for example.

The liver cell production method of the present invention may further include the step of maturing the liver cells in the presence of a liver cell maturation factor.

Examples of the liver cell maturation factor include oncostatin M (OSM), hepatocyte growth factor (HGF/scatter factor), dexamethasone, nicotinamide, dimethyl sulfoxide, and sodium butyrate. When the liver cell maturation factor is a protein, the source of the liver cell maturation factor may be the same as or different from the source of the liver cells, i.e., the source of the above-described pluripotent cells. One type of liver cell maturation factor may be used alone, or two or more types of liver cell maturation factors may be used in combination, for example. In the latter case, the combination of the liver cell maturation factors is not particularly limited, and examples thereof include: the combination of OSM and HGF; and the combination of OSM and dexamethasone. In the maturation of the liver cells, the same liver cell maturation factor may be used over the entire period, or different liver cell maturation factors may be used for respective predetermined periods. As to the predetermined periods, reference can be made to Examples etc. to be described below, for example.

The liver cells that have matured (also referred to as "mature liver cells" hereinafter) can be identified by the expression of a mature liver cell marker(s), such as a drug metabolism marker, a transporter markers, or a mature liver cell marker, for example. Examples of the drug metabolism marker include cytochrome P450, family 1, subfamily A, polypeptide 1 (CYP1A1), cytochrome P450 2C9 (CYP2C9), cytochrome P450 2C19 (CYP2C19), and cytochrome P450 3A4 (CYP3A4). Human-derived CYP1A1 has, as cDNA, the base sequence registered under NCBI Accession No. NM_000499, for example. Human-derived CYP2C9 has, as cDNA, the base sequence registered under NCBI Accession No. NM_000771, for example. Human-derived CYP2C19 has, as cDNA, the base sequence registered under NCBI Accession No. NM_000769, for example. Human-derived CYP3A4 has, as cDNA, the base sequence registered under NCBI Accession No. NM_001202855, for example. Examples of the transporter marker include multidrug resistance-associated protein 2 (MRP2), MDR/TAP (ABCB1, ATP-binding cassette, sub-family B [MDR/TAP], member 1), and UDP-glucuronosyltransferase 1-1 (UGT1A1). Human-derived MRP2 has, as cDNA, the base sequence registered under NCBI Accession No. NM_000392, for example. Human-derived MDR/TAP has, as cDNA, the base sequence registered under NCBI Accession No. NM_000927, for example. Human-derived UGT1A1 has, as cDNA, the base sequence registered under NCBI Accession No. NM_000463, for example. Examples of the mature liver cell marker include alpha-1 Antitrypsin (A1AT), tryptophan 2,3-dioxygenase (TDO2, TO), and albumin (ALB). Human-derived A1AT1 has, as cDNA, the base sequence registered under NCBI Accession No. NM_001127707, NM_001127706, NM_001127705, NM_001127704, NM_001127703, NM_001127702, NM_001127701, NM_001127700, NM_001002236, NM_001002235, or NM_000295, for example. Human-derived ALB has, as cDNA, the base sequence registered under NCBI Accession No. NM_000477, for example. In the liver cell production method of the present invention, cells expressing one type of mature liver cell marker may be identified as the mature liver cells, or cells expressing two or more types of mature liver cell markers may be identified as the mature liver cells, for example. Preferably, cells expressing all the mature liver cell markers are identified as the mature liver cells, because such mature liver cells have properties closer to those of mature liver cells in vivo. When TDO2 is used as the mature liver cell marker, it is preferable to use the TDO2 in combination with other mature liver cell marker(s).

In the maturation step, the maturation of the liver cells can be performed by culturing the liver cells in the presence of a culture solution (also referred to as "mature culture solution" hereinafter), for example. When the maturation of the liver cells is performed in the presence of the mature culture solution, the mature culture solution contains the liver cell maturation factor, for example. The mature culture solution is not particularly limited, and may be a liver cell culture solution, RPMI1640, DMEM, DMEM/F12, Iscove (IMEM), and αMEM, for example. Examples of the liver cell culture solution include a Hepatocyte basal medium BulletKit (LONZA). In the maturation of the liver cells, the same mature culture solution may be used over the entire period, or different mature culture solutions may be used for respective predetermined periods.

The mature culture solution may contain other components. As to the other components, reference can be made to the above description regarding the other components, for example.

In the maturation step, the maturation of the liver cells may be performed using feeder cells or without using feeder cells, for example. As to the feeder cell, reference can be made to the above description regarding the feeder cell, for example. When the maturation is performed without using the feeder cells, it is preferable to mature the liver cells on a scaffold in the maturation step, because this allows the resultant mature liver cells to have properties closer to those of mature liver cells in vivo. As to the scaffold, reference can be made to the above description regarding the scaffold, for example. In the maturation step, it is preferable to mature the liver cells on the extracellular matrix protein-containing coating, because this allows the resultant mature liver cells to have properties closer to those of mature liver cells in vivo.

In the maturation step, the liver cells obtained in the differentiation step may be used as they are, or the liver cells obtained in the differentiation step may be collected and the collected liver cells may be seeded, for example. When the liver cells are seeded, the cell density of the liver cells at the start of the maturation is not particularly limited, and may be, for example, from $1 \times 10^4$ to $2 \times 10^5$ cells/cm$^2$, preferably from $2.5 \times 10^4$ to $2 \times 10^5$ cells/cm$^2$, and more preferably from $5 \times 10^4$ to $1 \times 10^5$ cells/cm$^2$. The cell density can be calculated from the growth area of the culture vessel used for the maturation and the number of the cells, for example.

In the maturation step, the number of days for which the maturation of the liver cells is performed (also referred to as "maturation period" hereinafter) is not particularly limited, and is, for example, from 5 to 30 days, preferably from 7 to 18 days.

In the maturation step, the concentration of the liver cell maturation factor is not particularly limited, and may be from $1 \times 10^{-11}$ to $1 \times 10^{-7}$ mol/l, for example. The concentration of the liver cell maturation factor may be, for example, the concentration of one type of liver cell maturation factor or the sum of the concentrations of two or more types of liver cell maturation factors (the same applies hereinafter). When the liver cell maturation factor contains OSM, the concentration of the OSM is, for example, from $5 \times 10^{-10}$ to $1 \times 10^{-8}$ mol/l or $1 \times 10^{-9}$ to $5 \times 10^{-9}$ mol/l. When the liver cell maturation factor contains HGF, the concentration of the HGF is, for example, from $5 \times 10^{-10}$ to $1 \times 10^{-8}$ mol/l or $2 \times 10^{-9}$ to $1 \times 10^{-8}$ mol/l. When the liver cell maturation factor contains dexamethasone, the concentration of the dexamethasone is, for example, from $5 \times 10^{-9}$ to $1 \times 10^{-7}$ mol/l or $1 \times 10^{-8}$ to $1 \times 10^{-7}$ mol/l. When the liver cell maturation factor contains nicotinamide, the concentration of the nicotinamide is, for example, from $1 \times 10^{-4}$ to $1 \times 10^{-2}$ mol/l or $5 \times 10^{-3}$ to $2 \times 10^{-2}$ mol/l. When the liver cell maturation factor contains dimethyl sulfoxide, the concentration of the dimethyl sulfoxide is, for example, 0.001% to 1% (v/v) or 0.01% to 0.1% (v/v).

When the liver cell production method of the present invention includes the induction step, the combination of the cell density of the pluripotent cells at the start of the induction and the concentration of the liver cell maturation factor is not particularly limited. When the cell density of the pluripotent cells at the start of the induction is from $0.5 \times 10^4$ to $2 \times 10^5$ cells/cm$^2$, the concentration of the liver cell maturation factor is from $1 \times 10^{-11}$ to $1 \times 10^{-7}$ mol/l, for example.

The combination of the cell density of the endodermal cells at the start of the differentiation and the concentration of the liver cell differentiation factor is not particularly limited. When the cell density of the endodermal cells at the start of the differentiation is from $1 \times 10^4$ to $2 \times 10^5$ cells/cm$^2$, the concentration of the liver cell differentiation factor is from $1 \times 10^{-11}$ to $1 \times 10^{-7}$ mol/l, for example.

The combination of the cell density of the liver cells at the start of the maturation and the concentration of the liver cell maturation factor is not particularly limited. When the cell density of the liver cells at the start of the maturation is from $1 \times 10^4$ to $2 \times 10^5$ cells/cm$^2$, the concentration of the liver cell maturation factor is from $1 \times 10^{-11}$ to $1 \times 10^{-7}$ mol/l, for example.

In the maturation step, the culture conditions are not particularly limited, and the above description regarding the culture conditions in the induction step also applies to the culture conditions in the maturation step, for example.

It is preferable that, in the maturation step, the liver cells are matured in a microfluidic device. The microfluidic device includes: at least two openings; and a cell culture chamber, the openings communicate with the cell culture chamber, and during culture of liver cells on a scaffold to be carried out after introducing the liver cells and the scaffold into the cell culture chamber, the liver cell maturation factor can be supplied to the cell culture chamber through at least one of the openings while forming a concentration gradient in the cell culture chamber.

The device can be obtained by, for example, forming a template using a 3D printer or the like, then pouring a raw material onto the template, and hardening the raw material by polymerization or the like. The raw material is not particularly limited, and examples thereof include: polysiloxane polymers such as dimethylpolysiloxane (PDMS) and diphenylsiloxane, silicone resins/silicone rubbers, natural rubbers, synthetic rubbers, polyethylene terephthalate (PET), polymethyl methacrylate (PMMA), polymethyl acrylate (PMA), polycarbonates, polyolefins such as polyethylene and polypropylene, polyurethane, polystyrene, fluorinated polymers (PTFE, PVdF, etc.), polyvinyl chloride, polymethylhydrogensiloxane, homopolymers and copolymers such as a copolymer of dimethylsiloxane and methylhydrogensiloxane units, and mixtures thereof. Among them, polysiloxane polymers are preferable, and PDMS is more preferable. The device preferably has high transparency so as to allow easy evaluation of three-dimensional cell culture. Also, the device preferably has permeability to gases such as oxygen and carbon dioxide.

Figure 1B:
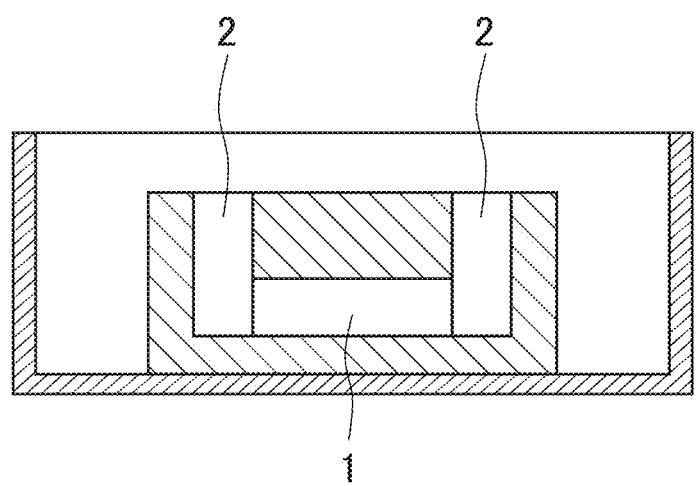
FIG. 1B is a schematic sectional view taken along line I-I' in FIG. 1A.

FIGS. 1A and 1B show an example of the device. FIG. 1A is a perspective view showing the configuration of a device 100 according to the present embodiment, and FIG. 1B is a schematic sectional view taken along line I-I' in FIG. 1A. As can be seen in FIGS. 1A and 1B, the device 100 of the present embodiment includes two cell culture chambers 1 and four openings 2. In the device 100, the number of the cell culture chambers 1 is not limited thereto, and may be one, or two or more. When the device is a high-throughput device, the number of the cell culture chambers may be from 10 to 400, for example. More specifically, the number of the cell culture chambers may be 16, 48, 96, or 384.

The size of each cell culture chamber 1 is not particularly limited, and may be as follows, for example: the length in the direction extending from one of the openings toward the other opening (the length direction) is from 1000 to 10000 μm; the width is from 100 to 1000 μm; and the height is from 100 to 1000 μm. The volume of each cell culture chamber 1 is not particularly limited, and is from 100 to 2000 μl, for example.

In the device 100 of the present embodiment, each cell culture chamber 1 communicates with the two openings 2 through which cells, culture solutions, and the like can be supplied, for example. With this configuration, replacement of culture solutions and supply of a liver cell maturation factor while forming a concentration gradient can be performed during culture of liver cells in the cell culture chamber 1, for example. Specifically, when a fresh culture solution is supplied through one of the openings in the cell culture chamber 1, the old culture solution is released through the other opening via the cell culture chamber 1, whereby the old culture solution is replaced with the fresh culture solution. In the present embodiment, the device 100 has two openings 2 for one cell culture chamber 1. It is to be noted, however, that the configuration of the device 100 is not limited thereto, and the device 100 may have three or more openings 2 for one cell culture chamber 1.

In the device 100, the openings 2 are cylindrical. It is to be noted, however, that the configuration of the device 100 is not limited thereto, and the openings 2 may have any shape. When the openings 2 are cylindrical, the size of each opening 2 is not particularly limited. The opening 2 may have a diameter from 100 to 3000 μm, for example, and a height from 2000 to 10000 μm, for example.

The device preferably is configured so that evaporation of culture solutions is prevented by putting a lid on an upper part thereof.

When the liver cell maturation factor is introduced into the opening 2, it forms a concentration gradient by, for example, diffusing inside the scaffold. The manner in which the liver cell maturation factor diffuses varies depending on the molecular weight of the liver cell maturation factor, for example.

The device preferably includes a narrow portion in the cell culture chamber, from the viewpoint of improving the efficiency of forming the concentration gradient of the liver cell maturation factor, for example. The shape of the narrow portion is not particularly limited. The narrow portion may have any shape such as a cylindrical shape, for example. When the narrow portion is cylindrical, the size of the narrow portion is not particularly limited. The narrow portion may have a diameter from 100 to 1000 μm, for example, and a length from 1000 to 10000 μm, for example. The narrow portion preferably has a smaller diameter than the openings, from the viewpoint of improving the efficiency of forming the concentration gradient of the liver cell maturation factor, for example. The position of the narrow portion in the cell culture chamber is not particularly limited. For example, the narrow portion may be at a central portion of the cell culture chamber, at the junction of the cell culture chamber and the opening, or at other positions.

When the device has three or more openings, two or more of them may communicate with the narrow portion, for example. With the configuration in which two or more of the openings communicate with the narrow portion, a plurality of liver cell maturation factors can be supplied to three-dimensional cultured cells at desired timings, for example.

When the liver cells are matured in the microfluidic device, the cell density of the liver cells at the start of the maturation is from $1\times10^1$ to $5\times10^6$ cells/cm². The cell density preferably is from $1\times10^3$ to $1\times10^5$ cells/cm², more preferably from $1\times10^4$ to $5\times10^4$ cells/cm², because this allows the mature liver cells obtained after the maturation step to form a three-dimensional structure. The cell density can be calculated from the area of the bottom surface of the cell culture chamber and the number of the cells, for example.

The differentiation step and the maturation step will be described below with reference to an example where activin A, BMP-4, and bFGF are used as the liver cell differentiation factors and OSM and HGF are used as the liver cell maturation factors. It is to be noted, however, that this example is merely illustrative and does not limit the present invention by any means.

First, endodermal cells are obtained by the endodermal cell production method of the present invention. Next, the endodermal cells suspended in a fifth culture solution were seeded in the culture vessel. The cell density of the endodermal cells at the start of differentiation is from $1\times10^4$ to $2\times10^5$ cells/cm², for example. The fifth culture solution is a differentiation culture solution containing $1\times10^{-10}$ to $1\times10^{-7}$ mol/l activin A, for example. The culture conditions are not particularly limited, and the $O_2$ partial pressure is, e.g., from 1% to 21%, and the $CO_2$ partial pressure is, e.g., from 5% to 6%. The culture temperature is from 36° C. to 37° C., for example. Under the above-described culture conditions, the cells are cultured for 1 to 5 days, for example.

Next, the fifth culture solution is removed, and a sixth culture solution is added. The sixth culture solution is a differentiation culture solution containing $1\times10^{-11}$ to $1\times10^{-9}$ mol/l BMP-4 and $1\times10^{-13}$ to $1\times10^{-11}$ mol/l FGF10, for example. Under the above-described culture conditions, the cells are cultured for 2 to 5 days, for example.

Next, the sixth culture solution is removed, and a seventh culture solution is added. The seventh culture solution is a mature culture solution containing $5\times10^{-10}$ to $1\times10^{-8}$ mol/l OSM and $5\times10^{-10}$ to $1\times10^{-8}$ mol/l HGF, for example. Under the above-described culture conditions, the cells are cultured for 2 to 25 days, for example.

Then, by collecting the cultured cells, mature liver cells can be obtained. When it is desired to obtain liver cells, the liver cells can be obtained by collecting the cultured cells after the culture of the cells in the sixth culture solution.

<Pancreatic Cell Production Method>

The pancreatic cell production method according to the present invention is, as described above, a pancreatic cell production method including the step of: differentiating endodermal cells into pancreatic cells in the presence of a pancreatic cell differentiation factor (the pancreatic cell differentiation step), wherein the endodermal cells are obtained by the endodermal cell production method according to the present invention. The pancreatic cell production method of the present invention is characterized in that the endodermal cells are obtained by the endodermal cell production method of the present invention, and other steps or conditions are not particularly limited. The pancreatic cell production method of the present invention can induce differentiation of pluripotent cells into pancreatic cells even when the pluripotent cells are dispersed and can achieve improved pancreatic cell production efficiency. The above description regarding the endodermal cell production method of the present invention also applies to the pancreatic cell production method of the present invention, for example.

The pancreatic cell production method of the present invention may include, prior to the pancreatic cell differentiation step, an induction step of inducing differentiation into endodermal cells by the endodermal cell production method of the present invention. The induction step can be carried out in the same manner as the induction step in the endodermal cell production method of the present invention, for example.

The pancreatic cell differentiation factor may be a keratinocyte growth factor (KGF), an epidermal growth factor (EGF), FGF2, FGF7, FGF10, a hedgehog signal inhibitor, a retinoic acid receptor (RAR) activator, Noggin, or an ALK inhibitor, for example. The RAR activator is not particularly limited, and may be a compound that activates RAR, for example. Examples of the compound that activates RAR include retinoid, 4-[(E)-2-(5,6,7,8-Tetrahydro-5,5,8,8-tetramethyl-2-naphthalenyl)-1-propenyl] benzoic acid (TTNPB), Tazarotene, Isotretinoin, Adapalene, AM 580, and EC 23. The RAR activator may activate any one, two or more, or all of RARα, RARβ, and RARγ, for example. The hedgehog signal inhibitor is not particularly limited, and may be, for example, cyclopamine or a derivative thereof, AY 9944 dihydrochloride, AZ 12080282 dihydrochloride, GANT 58, GANT 61, or HPI 1. The cyclopamine derivative may be 3-Keto-N-aminoethyl-N'-aminocaproyldihydrocinnamoyl cyclopamine (KAAD-CYC), for example. The ALK (anaplastic lymphoma receptor tyrosine kinase) inhibitor is not particularly limited, and may be SB432541, for example. When the pancreatic cell differentiation factor is a protein, the source of the pancreatic cell differentiation factor may be the same as or different from the source of the endodermal cells, i.e., the source of the above-described pluripotent cells. One type of pancreatic cell differentiation factor may be used alone, or two or more types of pancreatic cell differentiation factors may be used in combination, for example. In the latter case, the combination of the pancreatic cell differentiation factors is not particularly limited, and examples thereof include: the combination of the hedgehog signal inhibitor, the RAR activator, and Noggin; and the combination of KGF, Noggin, and EGF. In the differentiation of the endodermal cells into the pancreatic cells, the same pancreatic cell differentiation factor may be used over the entire period, or different pancreatic cell differentiation factors may be used for respective predetermined periods. As to the predetermined periods, reference can be made to Examples etc. to be described below, for example.

The pancreatic cells can be identified by the expression of a pancreatic cell marker(s), for example. Examples of the pancreatic cell marker include insulin, pancreas specific transcription factor 1a (PTF1α), homeobox protein Nkx-6.1 (NKX6.1), pancreatic and duodenal homeobox 1 (PDX1), musculoaponeurotic fibrosarcoma oncogene family A (MAFA), musculoaponeurotic fibrosarcoma oncogene family B (MAFB), glucose transporter 2 (GLUT2, solute carrier family 2 [facilitated glucose transporter], member 2 (SLC2A2)), and solute carrier family 30 (zinc transporter), member 8 (SLC30A8). Human-derived insulin has, as cDNA, the base sequence registered under NCBI Accession No. NM_000207, for example. Human-derived PTF1α has, as cDNA, the base sequence registered under NCBI Accession No. NM_178161, for example. Human-derived NKX6.1 has, as cDNA, the base sequence registered under NCBI Accession No. NM_006168, for example. Human-derived PDX1 has, as cDNA, the base sequence registered under NCBI Accession No. NM_000209, for example. Human-derived MAFA has, as cDNA, the base sequence registered under NCBI Accession No. NM_201589.3, for example. Human-derived MAFB has, as cDNA, the base sequence registered under NCBI Accession No. NM_005461.4, for example. Human-derived GLUT2 has, as cDNA, the base sequence registered under NCBI Accession No. NM_000340, for example. Human-derived SLC30A8 has, as cDNA, the base sequence registered under NCBI Accession No. NM_001172811, for example. In the pancreatic cell production method of the present invention, cells expressing one type of pancreatic cell marker may be identified as the pancreatic cells, or cells expressing two or more types of pancreatic cell markers may be identified as the pancreatic cells, for example. Preferably, cells expressing all the pancreatic cell markers are identified as the pancreatic cells, because such pancreatic cells have properties closer to those of pancreatic cells in vivo.

In the pancreatic cell differentiation step, the differentiation of the endodermal cells into the pancreatic cells can be performed by culturing the endodermal cells in the presence of a culture solution (also referred to as "pancreatic cell differentiation culture solution" hereinafter), for example. When the differentiation into the pancreatic cells is performed in the presence of the pancreatic cell differentiation culture solution, the pancreatic cell differentiation culture solution contains the pancreatic cell differentiation factor, for example. The pancreatic cell differentiation culture solution is not particularly limited, and may be an RPMI1640 medium, DMEM, DMEM/F12, Iscove (IMEM), or αMEM, for example. In the differentiation of the endodermal cells into the pancreatic cells, the same pancreatic cell differentiation culture solution may be used over the entire period, or different pancreatic cell differentiation culture solutions may be used for respective predetermined periods. As to the predetermined periods, reference can be made to Examples etc. to be described below, for example.

The pancreatic cell differentiation culture solution also may contain other components. As to the other components, reference can be made to the above description regarding the other components, for example.

In the pancreatic cell differentiation step, the differentiation of the endodermal cells into the pancreatic cells may be performed using feeder cells or without using feeder cells, for example. As to the feeder cells, reference can be made to the above description regarding the feeder cells, for example. When the differentiation is performed without using the feeder cells, it is preferable to mature the endodermal cells on a scaffold. As to the scaffold, reference can be made to the above description regarding the scaffold, for example.

In the pancreatic cell differentiation step, the endodermal cells are not limited as long as they are endodermal cells obtained by the endodermal cell production method of the present invention. When the pancreatic cell production method of the present invention includes the induction step, the endodermal cells obtained in the induction step may be used as they are, or the endodermal cells obtained in the induction step may be collected and the collected endodermal cells may be seeded, for example. When the endodermal cells are seeded, the cell density of the endodermal cells at the start of the differentiation is not particularly limited, and may be, for example, $1\times10^4$ to $2\times10^5$ cells/cm$^2$, $2.5\times10^4$ to $2\times10^5$ cells/cm$^2$, or $5\times10^4$ to $1\times10^5$ cells/cm$^2$. The cell density can be calculated from the growth area of the culture vessel used for the differentiation and the number of the cells, for example.

In the pancreatic cell differentiation step, the number of days for which differentiation of the endodermal cells into the pancreatic cells is performed (also referred to as "pancreatic cell differentiation period" hereinafter) is not particularly limited, and is, for example, from 7 to 21 days, preferably from 9 to 14 days.

In the pancreatic cell differentiation step, the concentration of the pancreatic cell differentiation factor is not particularly limited, and may be from $1\times10^{-4}$ to $5\times10^{-5}$ mol/l, for example. The concentration of the pancreatic cell differentiation factor may be, for example, the concentration of one type of pancreatic cell differentiation factor or the sum of the concentrations of two or more types of pancreatic cell differentiation factors (the same applies hereinafter). When the pancreatic cell differentiation factor contains KGF, the concentration of the KGF is from $1\times10^{-10}$ to $5\times10^{-7}$ mol/l or $1\times10^{-9}$ to $5\times10^{-8}$ mol/l, for example. When the pancreatic cell differentiation factor contains EGF, the concentration of the EGF is from $1\times10^{-8}$ to $5\times10^{-4}$ mol/l or $1\times10^{-7}$ to $5\times10^{-5}$ mol/l, for example. When the pancreatic cell differentiation factor contains a hedgehog signal inhibitory substance, the concentration of the hedgehog signal inhibitor is from $1\times10^{-11}$ to $1\times10^{-7}$ mol/l or $1\times10^{-10}$ to $1\times10^{-8}$ mol/l, for example. When the pancreatic cell differentiation factor contains an RAR activator, the concentration of the RAR activator is from $1\times10^{-7}$ to $1\times10^{-4}$ mol/l or $5\times10^{-7}$ to $1\times10^{-5}$ mol/l, for example. When the pancreatic cell differentiation factor contains Noggin, the concentration of the Noggin is from $1\times10^{-10}$ to $1\times10^{-7}$ mol/l or $1\times10^{-9}$ to $1\times10^{-8}$ mol/l, for example.

When the pancreatic cell production method of the present invention includes the induction step, the combination of the cell density of the pluripotent cells at the start of the induction and the concentration of the pancreatic cell differentiation factor is not particularly limited. When the cell density of the pluripotent cells at the start of the induction is from $0.5\times10^4$ to $2\times10^5$ cells/cm$^2$, the concentration of the pancreatic cell differentiation factor is from $1\times10^{-4}$ to $5\times10^{-5}$ mol/l, for example.

The combination of the cell density of the endodermal cells at the start of the pancreatic cell differentiation and the concentration of the pancreatic cell differentiation factor is not particularly limited. When the cell density of the endodermal cells at the start of the differentiation is from $1\times10^4$ to $2\times10^5$ cells/cm$^2$, the concentration of the pancreatic cell differentiation factor is from $1\times10^{-4}$ to $5\times10^{-5}$ mol/l, for example.

In the pancreatic cell differentiation step, the culture conditions are not particularly limited, and the above description regarding the culture conditions in the induction step also applies to the culture conditions in the differentiation step, for example.

The pancreatic cell differentiation step will be described below with reference to an example where KGF, a hedgehog signal inhibitor, an RAR activator, Noggin, and EGF are used as the pancreatic cell differentiation factors. It is to be noted, however, that this example is merely illustrative and does not limit the present invention by any means.

First, endodermal cells are obtained by the endodermal cell production method of the present invention. Next, the endodermal cells suspended in an eighth culture solution were seeded in the culture vessel. The cell density of the endodermal cells at the start of differentiation is from $1\times10^4$ to $2\times10^5$ cells/cm$^2$, for example. The seventh culture solution is a pancreatic cell differentiation culture solution containing $1\times10^{-10}$ to $5\times10^{-7}$ mol/l KGF, for example. The culture conditions are not particularly limited, and the $O_2$ partial pressure is, e.g., from 1% to 21%, and the $CO_2$ partial pressure is, e.g., from 5% to 6%. The culture temperature is from 36° C. to 37° C., for example. Under the above-described culture conditions, the cells are cultured for 2 to 5 days, for example.

Next, the eighth culture solution is removed, and a ninth culture solution is added. The ninth culture solution is a pancreatic cell differentiation culture solution containing $1\times10^{-11}$ to $1\times10^{-7}$ mol/l hedgehog signal inhibitor, $1\times10^{-7}$ to $1\times10^{-4}$ mol/l RAR activator, and $1\times10^{-10}$ to $1\times10^{-7}$ mol/l Noggin, for example. Under the above-described culture conditions, the cells are cultured for 3 to 9 days for example.

Next, the ninth culture solution is removed, and a tenth culture solution is added. The tenth culture solution is a pancreatic cell differentiation culture solution containing $1\times10^{-10}$ to $5\times10^{-7}$ mol/l KGF, $1\times10^{-10}$ to $1\times10^{-7}$ mol/l Noggin, and $1\times10^{-8}$ to $5\times10^{-4}$ mol/l EGF, for example. Under the above-described culture conditions, the cells are cultured for 3 to 9 days, for example.

Then, by collecting the cultured cells, pancreatic cells can be obtained. After the culture of the cells in the ninth culture solution, the endodermal cells in the process of differentiating may be collected from the culture vessel and reseeded in another culture vessel. The cell density of the endodermal cells at the time of reseeding is from $6\times10^4$ to $4.8\times10^5$ cells/cm$^2$, for example. In this case, it is preferable to inhibit the ROCK activity during the culture of the cells in the tenth culture solution. Specifically, to this end, the tenth culture solution contains the ROCK activity inhibitor, for example. The concentration of the ROCK activity inhibitor in the tenth culture solution is from $1\times10^{-6}$ to $1\times10^{-4}$ mold, for example.

<Cells Obtained by the Production Methods>

The endodermal cells of the present invention are characterized in that they are obtained by the endodermal cell production method of the present invention. The liver cells of the present invention are characterized in that they are obtained by the liver cell production method of the present invention. The pancreatic cells of the present invention are characterized in that they are obtained by the pancreatic cell production method of the present invention. The above descriptions regarding the endodermal cell production method, the liver cell production method, and the pancreatic cell production method of the present invention also apply to the endodermal cells, the liver cells, and the pancreatic cells of the present invention, respectively.

<Endodermal Cell Induction Promoter>

The endodermal cell induction promoter of the present invention is, as described above, an endodermal cell induction promoter containing a ROCK protein activity inhibitor. The endodermal cell induction promoter of the present invention is characterized in that it contains the ROCK protein activity inhibitor, and other configurations or conditions are not particularly limited. The endodermal cell induction promoter of the present invention can induce differentiation of pluripotent cells into endodermal cells even when the pluripotent cells are dispersed and can achieve improved endodermal cell production efficiency. The above descriptions regarding the endodermal cell production method etc. of the present invention also apply to the endodermal cell induction promoter of the present invention, for example.

The endodermal cell induction promoter of the present invention may further contain the above-described endodermal cell inducing factor(s).

In the endodermal cell induction promoter of the present invention, the respective constituent components may be contained in different containers, or they may be contained in the same container either in a mixed or unmixed state. When the respective constituent components are contained in different containers, the endodermal cell induction promoter of the present invention also can be referred to as an endodermal cell induction promoting kit.

The endodermal cell induction promoter of the present invention may further contain constituent components other than the ROCK activity inhibitor. Examples of the other constituent components include a culture vessel and instructions for use. The culture vessel is not particularly limited, and may be a known cell culture vessel, for example.

<Liver Cell Induction Promoting Kit>

The liver cell induction promoting kit of the present invention is, as described above, a liver cell induction promoting kit including the endodermal cell induction promoter according to the present invention. The liver cell induction promoting kit of the present invention is characterized in that it includes the endodermal cell induction promoter of the present invention, and other configurations or conditions are not particularly limited. The liver cell induction promoting kit of the present invention can induce differentiation of pluripotent cells into liver cells even when the pluripotent cells are dispersed and can achieve improved liver cell production efficiency. The above descriptions regarding the endodermal cell production method, the liver cell production method, the endodermal cell induction promoter, etc. of the present invention also apply to the liver cell induction promoting kit of the present invention, for example.

The liver cell induction promoting kit of the present invention may further include the above-described liver cell differentiation factor(s). The liver cell induction promoting kit of the present invention may further include the above-described liver cell maturation factor(s).

In the liver cell induction promoting kit of the present invention, the respective constituent components may be contained in different containers, or they may be contained the same container either in a mixed or unmixed state. When the respective constituent components are contained in the same container in a mixed or unmixed state, the liver cell induction promoting kit of the present invention also can be referred to as a liver cell induction promoter.

The liver cell induction promoting kit of the present invention may further include constituent components other than the endodermal cell induction promoter of the present invention. Examples of the constituent other components include the above-described culture vessel, the above-described microfluidic device, and instructions for use.

<Pancreatic Cell Induction Promoting Kit>

The pancreatic cell induction promoting kit of the present invention is, as described above, a pancreatic cell induction promoting kit including the endodermal cell induction promoter according to the present invention. The pancreatic cell induction promoting kit of the present invention is characterized in that it includes the endodermal cell induction promoter of the present invention, and other configurations or conditions are not particularly limited. The pancreatic cell induction promoting kit of the present invention can induce differentiation of pluripotent cells into pancreatic cells even when the pluripotent cells are dispersed and can achieve improved pancreatic cell production efficiency. The above descriptions regarding the endodermal cell production method, the pancreatic cell production method, the endodermal cell induction promoter, the liver cell induction promoting kit, etc. of the present invention also apply to the pancreatic cell induction promoting kit of the present invention, for example.

The pancreatic cell induction promoting kit of the present invention may further include the above-described pancreatic cell differentiation factor(s).

In the pancreatic cell induction promoting kit of the present invention, the respective constituent components may be contained in different containers, or they may be contained in the same container either in a mixed or unmixed state. When the respective constituent components are contained in the same container in a mixed or unmixed state, the pancreatic cell induction promoting kit of the present invention also can be referred to as a pancreatic cell induction promoter.

The pancreatic cell induction promoting kit of the present invention may further include constituent components other than the endodermal cell induction promoter of the present invention. Examples of the other constituent components include a culture vessel and instructions for use. The culture vessel is not particularly limited, and may be a known cell culture vessel, for example.

<Microfluidic Device>

The microfluidic device of the present invention is a microfluidic device for use in the liver cell production method of the present invention, including; at least two openings; and a cell culture chamber, the openings communicating with the cell culture chamber, wherein, during culture of liver cells on a scaffold to be carried out after introducing the liver cells and the scaffold into the cell culture chamber, a liver cell maturation factor can be supplied to the cell culture chamber through at least one of the openings while forming a concentration gradient in the cell culture chamber. The microfluidic device of the present invention is characterized in that it is used in the liver cell production method according to the present invention, and other configurations or conditions are not particularly limited. The above descriptions regarding the endodermal cell production method etc. of the present invention also apply to the microfluidic device of the present invention, for example. According to the microfluidic device of the present invention, three-dimensional liver cells can be produced, for example.

EXAMPLES

The present invention will be described specifically below with reference to examples. It is to be noted, however, that the present invention is by no means limited to embodiments described in the following examples.

Example 1

The present example was conducted to demonstrate, using different types of culture solutions, that endodermal cells can be produced from dispersed pluripotent cells and pluripotent cells forming cell clusters by inhibiting ROCK activity and that the endodermal cells can be produced with high differentiation efficiency.

(1) Production of Endodermal Cells (Culture Day 1)

On a 24-well dish (growth area: 1.9 cm$^2$/well, BD Falcon [trademark]), a H9 cell line (obtained from WiCell), which is a human ES cell, was seeded in a dispersed state at a cell density of 1×10⁵ cells/well and cultured for 24 hours. The culture conditions were set as follows: 37° C. and 5% $CO_2$. As a culture solution, mTeSR-1 (STEMCELL) containing 10 μmol/l Y27632 (ROCK activity inhibitory compound, Wako) and 100 ng/ml activin A (R&D Systems) was used. To the mTeSR-1A, a penicillin-streptomycin solution (Wako) had been added beforehand so that the mTeSR-1 contained 100 U/ml penicillin and 100 U/ml streptomycin.

(Culture Day 2)

After the culture, the culture solution used on culture day 1 was removed, and a culture solution with the same composition was further added to each well. The cells were further cultured for one day under the above-described culture conditions.

(Culture Day 3)

The culture solution used on culture day 2 was removed, and mTeSR-1 containing 10 μmol/l Y27632, 100 ng/ml activin A, 10 ng/ml BMP-4 (R&D Systems), 10 μmol/l LY294002 (PI₃K activity inhibitory compound, CAYMAN CHEMICAL COMPANY), and 3 μmol/l CHIR99021 (GSK-3β activity inhibitory compound, STEMGENT) was added. Then, the cells were cultured for 24 hours under the above-described culture conditions.

(Culture Day 4)

The culture solution used on culture day 3 was removed, and mTeSR-1 containing 10 μmol/l Y27632, 100 ng/ml activin A, 10 ng/ml BMP-4, and 10 μmol/l LY294002 was added. Then, the cells were cultured for 24 hours under the above-described culture conditions.

(Culture Day 5)

The culture solution used on culture day 4 was removed, and an RPMI/B-27 culture solution containing 100 ng/ml activin A and 10 ng/ml BMP-4 was added. Then, the cells were cultured for 24 hours under the above-described culture conditions. The RPMI/B-27 culture solution had the composition shown in Table 1 below.

TABLE 1

| | |
|---|---|
| RPMI1640 (containing GlutaMAX [trademark]) (GIBCO) | 490 ml |
| B-27 ® supplement (GIBCO) | 10 ml |
| Non-essential amino acid solution (NEAA, Sigma) | 5 ml |
| Penicillin/streptomycin solution (Wako) | 5 ml |
| Total | 510 ml |

(2) CXCR4 Expression

After the culture on culture day 5, the cells were collected from each well. Then, the cells were stained with an APC-labeled anti-human CXCR4 antibody (clone name: 12G5, BD Pharmigen). CXCR4 expression in the stained cells was measured using a flow cytometer (BD FACSCanto [trademark] II, BD Biosciences). CXCR4 expression was also measured in the same manner, except that, from culture day 1 to culture day 4, TeSR-E8 or CDM-PVA was used instead of the mTeSR-1. Further, CXCR4 expression was measured in the same manner, except that, instead of the H9 cell line in the dispersed state, the H9 cell line forming cell clusters was seeded on culture day 1. As a control, CXCR4 expression was measured in the same manner, except that an APC-labeled control antibody (clone name: G155-178, BD Pharmigen) was used instead of the anti-human CXCR4 antibody.

Figure 2:
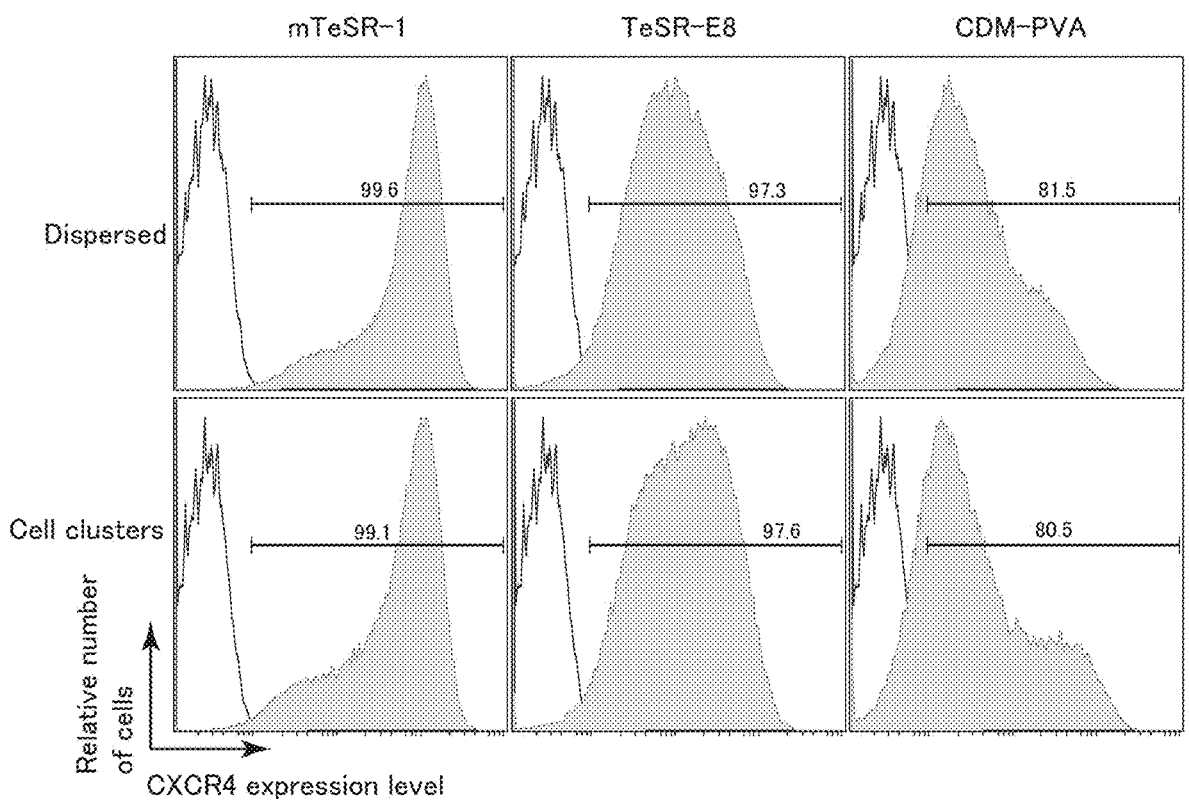
FIG. 2 shows histograms showing the expression levels of CXCR4 in Example 1.

The results obtained are shown in FIG. 2. FIG. 2 shows histograms each showing the CXCR4 expression level. In FIG. 2, the horizontal axis indicates the CXCR4 expression level, the vertical axis indicates the relative number of the cells, and the number in each histogram indicates the proportion of the endodermal cells. In FIG. 2, the histograms in the upper row show the results obtained when differentiation of the dispersed pluripotent cells was induced. The histograms in the lower row show the results obtained when differentiation of the pluripotent cells forming cell clusters was induced. The shaded histograms show the results obtained regarding the present example, and the open histograms show the results obtained regarding the control. In FIG. 2, the histograms show, from the left, the results obtained when the mTeSR-1, the TeSR-E8, and the CDM-PVA were used, respectively. As can be seen in FIG. 2, the proportion of the cells positive to the endoderm cell marker CXCR4 was 80.5% or more under any of these conditions. Also, comparison of the respective culture solutions revealed that the proportion of the CXCR4 strongly positive-endodermal cells was higher in the order of the mTeSR-1, the TesR-E8, and the CDM-PVA. These results demonstrate that, by inhibiting ROCK activity, endodermal cells can be produced from dispersed pluripotent cells and pluripotent cells forming cell clusters with high differentiation efficiency. These results also demonstrate that the endodermal cell production method of the present invention can induce differentiation of pluripotent cells into endodermal cells even when the pluripotent cells are dispersed. Furthermore, the fact that the mTeSR-1 and the TeSR-E8 exhibited higher differentiation efficiencies than the CDM-PVA demonstrates that the efficiency of endodermal cell production can be improved further by using a medium containing a TGF-β family protein and bFGF.

Example 2

In the present example, pluripotent cells were seeded at different cell densities at the start of induction to examine whether endodermal cells can be produced with high differentiation efficiency and whether SOX17 as an endodermal cell marker is expressed in the cells obtained after the induction.

(1) Production of Endodermal Cells

Differentiation into endodermal cells was induced in the same manner as in Example 1, except that the H9 cell line was seeded at a cell density of 5×10⁴ cells/well, 1×10⁵ cells/well, or 2×10⁵ cells/well. Also, differentiation into endodermal cells was induced in the same manner, except that, instead of the H9 cell line in the dispersed state, a H9 cell line forming cell clusters was seeded. Then, the endodermal cells obtained after the induction were collected.

(2) CXCR4 Expression

CXCR4 expression in the thus-obtained endodermal cells was measured in the same manner as in (2) in Example 1. As a control, CXCR4 expression was measured in the same manner, except that the APC-labeled control antibody was used instead of the anti-human CXCR4 antibody.

Figure 3:
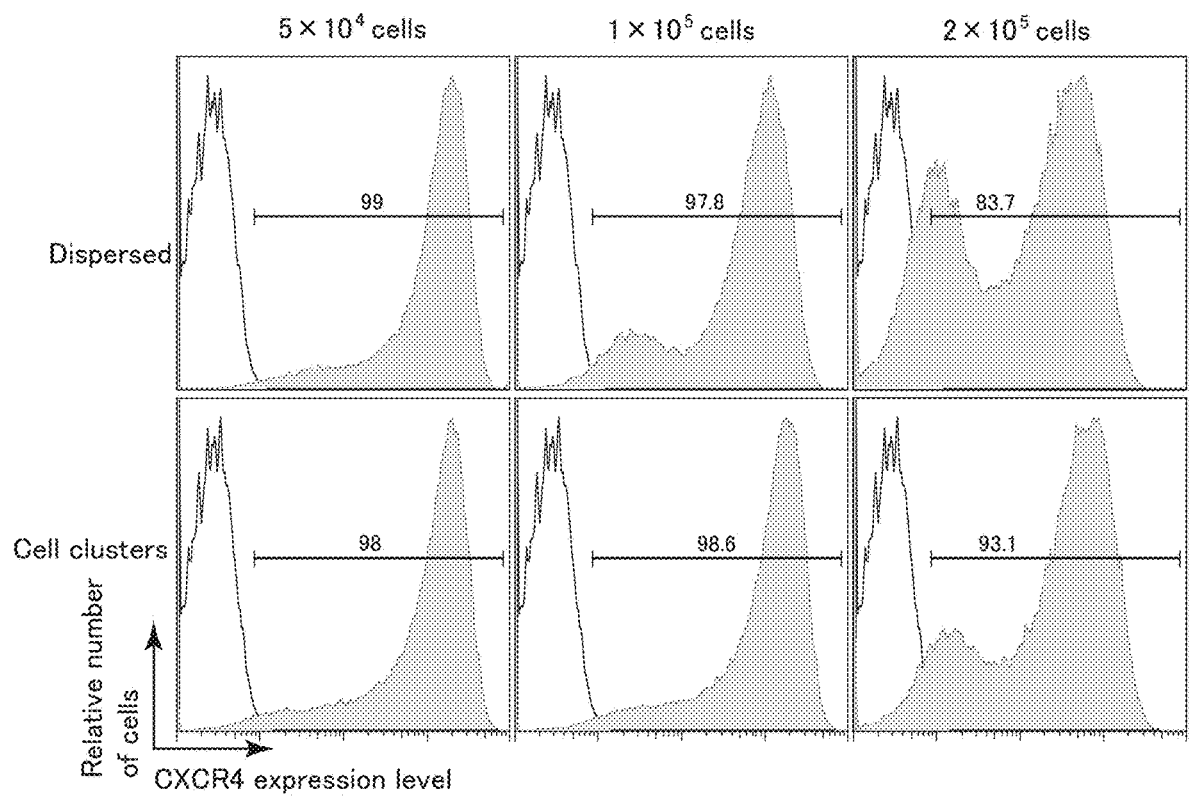
FIG. 3 shows histograms showing the expression levels of CXCR4 in Example 2.

The results obtained are shown in FIG. 3. FIG. 3 shows histograms each showing the CXCR4 expression level. In FIG. 3, the horizontal axis indicates the CXCR4 expression level, the vertical axis indicates the relative number of the cells, and the number in each histogram indicates the proportion of the endodermal cells. In FIG. 3, the histograms in the upper row show the results obtained when differentiation of the dispersed pluripotent cells was induced. The histograms in the lower row show the results obtained when differentiation of the pluripotent cells forming cell clusters was induced. The shaded histograms show the results obtained regarding the present example, and the open histograms show the results obtained regarding the control. In FIG. 3, the histograms show, from the left, the results obtained when the H9 cell line was seeded at the cell density of $5\times10^4$ cells/well, $1\times10^5$ cells/well, and $2\times10^5$ cells/well, respectively. As can be seen in FIG. 3, the proportion of the cells positive to the endoderm cell marker CXCR4 was 83.7% or more under any of these conditions. Also, comparison of the cell densities of the pluripotent cells at the start of the induction revealed that the proportion of the CXCR4 positive endodermal cells was higher in the cases where the cell densities were $5\times10^4$ cells/well and $1\times10^5$ cells/well as compared with the case where the cell density was $2\times10^5$ cells/well. Furthermore, the proportion of the CXCR4 strongly positive-endodermal cells was higher in the order of the cell densities of $5\times10^4$ cells/well, $1\times10^5$ cells/well, and $2\times10^5$ cells/well. These results demonstrate that the efficiency of endodermal cell production can be improved further by setting the cell density of the pluripotent cells at the start of the induction low (specifically, $1\times10^4$ to $7\times10^4$ cells/cm$^2$, more preferably $2\times10^4$ to $6\times10^4$ cells/cm$^2$).

(3) The Number of the Produced Cells

The endodermal cells obtained in (1) above were counted.

Figure 4:
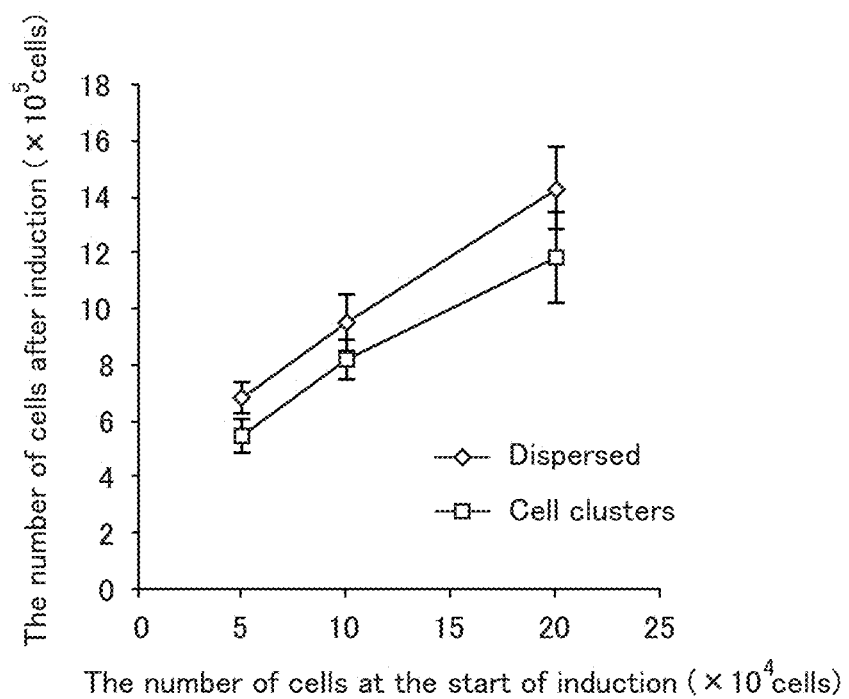
FIG. 4 is a graph showing the number of cells in Example 2.

The results obtained are shown in FIG. 4. FIG. 4 is a graph showing the number of the cells. In FIG. 4, the horizontal axis indicates the number of the cells of the H9 cell line at the start of the induction, and the vertical axis indicates the number of the endodermal cells obtained after the induction. In FIG. 4, the rhombuses (◇) indicate the results obtained when the differentiation of the dispersed pluripotent cells was induced, and the open squares (□) indicate the result obtained when the differentiation of the pluripotent cells forming cell clusters was induced. As can be seen in FIG. 4, under any of these conditions, the number of the endodermal cells obtained after the induction was at least six times greater than the number of the cells of the H9 cell line at the start of the induction. Also, comparison of the dispersed states at the start of the induction revealed that the number of the endodermal cells obtained after the induction when the dispersed pluripotent cells were used was greater than that when the pluripotent cells forming cell clusters dispersed pluripotent cells were used. These results demonstrate that the endodermal cell production method of the present invention can produce endodermal cells with high production efficiency, regardless of the dispersed state of the pluripotent cells at the start of induction. These results also demonstrate that the efficiency of endodermal cell production can be improved further by seeding dispersed pluripotent cells.

(4) SOX17 Gene Expression

RNA was extracted from the endodermal cells obtained in (1) above by an ordinary method. Then, using a reverse transcriptase and a random primer, cDNA was synthesized from the RNA by an ordinary method. With the thus-obtained cDNA as a template, quantitative RT-PCR was performed using a PCR reagent (TaKaRa Taq [trademark] [with Mg$^{2+}$ free Buffer], Takara Bio), a real-time (RT)-PCR reagent (Power SYBR® Green PCR Master Mix, ABI), and an Applied Biosystems® 7500 real-time PCR system (Life Technologies) in accordance with the protocols attached thereto. The mRNA expression level of the SOX17 gene and the mRNA expression level of the GAPDH gene (an internal standard) in the RNA were measured. The mRNA expression level of the SOX17 gene was calculated as the ratio thereof to the mRNA expression level of the GAPDH gene. In the qRT-PCR, the following primer sets were used for the amplification of the SOX17 gene and the GAPDH gene, respectively.

Primer Set for SOX17 Gene Amplification (SEQ ID NO: 1)
5'-CGCACGGAATTTGAACAGTA-3'

(SEQ ID NO: 2)
5'-GGATCAGGGACCTGTCACAC-3'

Primer Set for GAPDH Gene Amplification (SEQ ID NO: 3)
5'-ACCACAGTCCATGCCATCAC-3'

(SEQ ID NO: 4)
5'-TCCACCACCCTGTTGCTGTA-3'

Figure 5:
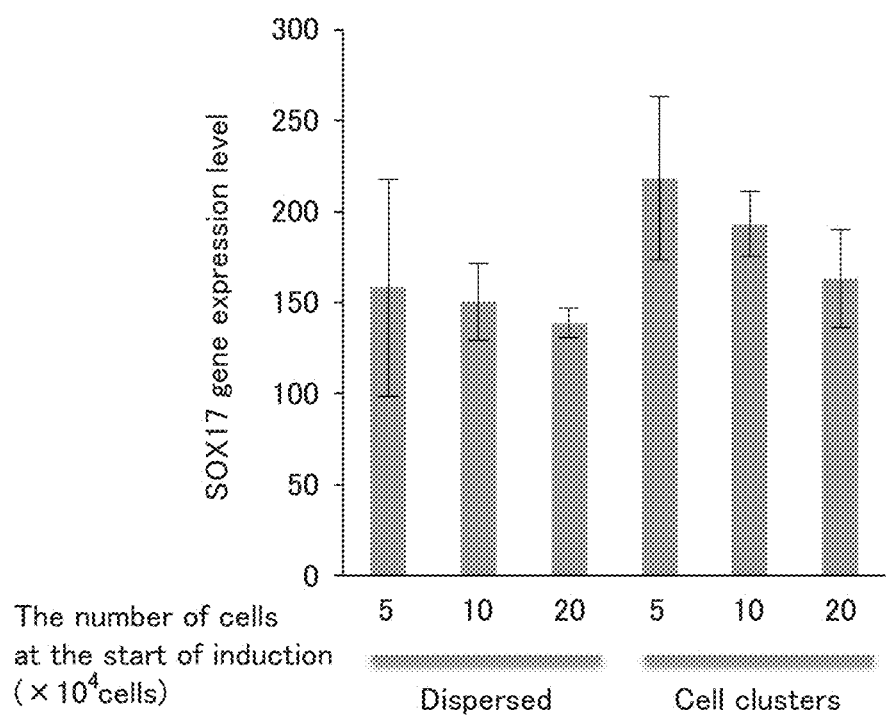
FIG. 5 is a graph showing the expression levels of the SOX17 gene in Example 2.

The results obtained are shown in FIG. 5. FIG. 5 is a graph showing the expression level of the SOX17 gene. In FIG. 5, the horizontal axis indicates the cell density of the pluripotent cells and the dispersed state at the start of the induction, and the vertical axis indicates the expression level of the SOX17 gene. As can be seen in FIG. 5, the expression of the SOX17 gene was observed under any of these conditions. Also, comparison of the dispersed states at the start of the induction revealed that the expression level of the SOX17 gene observed when the pluripotent cells forming cell clusters were used was higher than the expression level of the SOX17 gene observed when the dispersed pluripotent cells were used. These results demonstrate that differentiation into endoderm cells can be induced by the endodermal cell production method of the present invention.

Example 3

The present example was conducted to demonstrate that liver cells can be produced from dispersed pluripotent cells and pluripotent cells forming cell clusters by inhibiting ROCK activity.

(1) Production of Endodermal Cells

Differentiation into endodermal cells was induced in the same manner as in Example 1, except that the H9 cell line was seeded at a cell density of $5\times10^4$ cells/well, $1\times10^5$ cells/well, or $2\times10^5$ cells/well. Also, differentiation into endodermal cells was induced in the same manner, except that, instead of the H9 cell line in the dispersed state, a H9 cell line forming cell clusters was seeded.

(2) Production of Liver Cells (Culture Day 6 to Culture Day 8)

The culture solution used on culture day 5 was removed, and a RPMI/B-27 culture solution containing 50 ng/ml activin A was added. Then, the cells were cultured for 3 days under the above-described culture conditions. During the culture for 3 days, the culture solution in the wells was replaced daily with a fresh culture solution having the same composition.

(Culture Day 9 to Culture Day 12)

The culture solution used on culture day 8 was removed, and a RPMI/B-27 culture solution containing 20 ng/ml BMP-4 and 10 ng/ml human FGF10 (R&D Systems) was added. Then, the cells were cultured for 4 days under the above-described culture conditions. During the culture for 4 days, the culture solution in the wells was replaced daily with a fresh culture solution having the same composition.

(3) Expression of Liver Cell Markers

After the culture on culture day 12, the cells were collected from each well. Then, cDNA was synthesized in the same manner as in (4) in Example 2, except that the collected cells were used instead of the endodermal cells. Thereafter, with the thus-obtained cDNA as a template, PCR was performed using the above-described PCR reagent and a thermal cycler (Mastercycler® pro, Eppendorf AG) in accordance with the protocols attached thereto, thereby amplifying the AFP gene, the HNF4α gene, and the GAPDH gene in the RNA. The PCR solution after the amplification was applied to electrophoresis using 1.8% agarose gel. After the electrophoresis, the gel was stained with Gel Red™ (Biotium), and the expression of the AFP gene, the HNF4α gene, and the GAPDH gene was examined. In the PCR, the following primer sets were used for the amplification of the AFP gene and the HNF4α gene, respectively. As a positive control, the expression of the AFP gene, the HNF4α gene, and the GAPDH gene was examined in the same manner, except that HepG2 cells (obtained from ATCC), which are a human liver cancer-derived cell line expressing the AFP gene and the HNF4α gene, were used instead of the collected cells. As a negative control, the expression of the AFP gene, the HNF4α gene, and the GAPDH gene was examined in the same manner, except that the cDNA was not added.
Primer Set for AFP Gene Amplification

```
                                      (SEQ ID NO: 5)
5'-AAATGCGTTTCTCGTTGCTT-3'

(SEQ ID NO: 6)
5'-GCCACAGGCCAATAGTTTGT-3'
```

Primer Set for HNF4α Gene Amplification

```
                                      (SEQ ID NO: 7)
5'-CCACGGGCAAACACTACGG-3'

(SEQ ID NO: 8)
5'-GGCAGGCTGCTGTCCTCAT-3'
```

Figure 6:
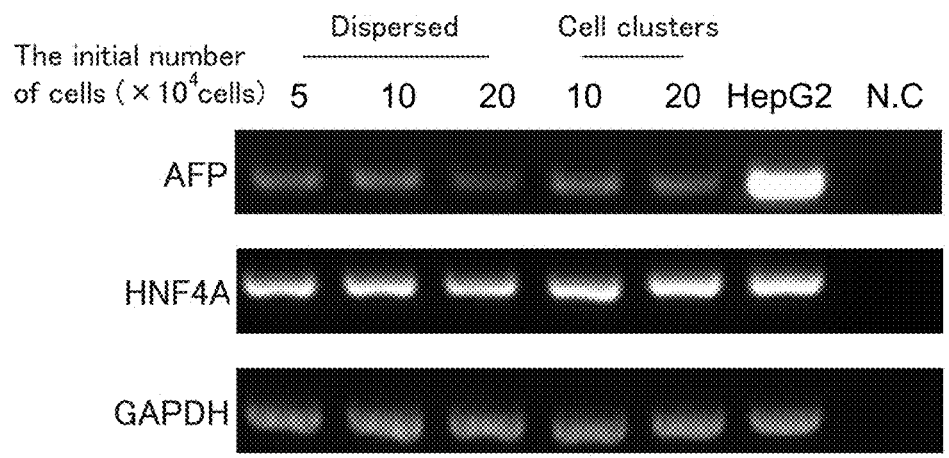
FIG. 6 shows photographs indicating the expression of the AFP gene, the HNF4α gene, and the GAPDH gene in Example 3.

The results obtained are shown in FIG. 6. FIG. 6 shows photographs indicating the expression of the AFP gene, the HNF4α gene, and the GAPDH gene. In FIG. 6, the types of the samples are indicated above the photographs, the type of the gene is indicated on the left of each photograph, and the respective lanes indicate, from the left, the results obtained when the H9 cell line in the dispersed state was seeded at the cell densities of 5×10$^4$ cells/well, 1×10$^5$ cells/well, and 2×10$^5$ cells/well, the results obtained when the H9 cell line forming cell clusters was seeded at the cell densities of 1×10$^5$ cells/well and 2×10$^5$ cells/well, and the results obtained regarding the positive control and the negative control. As can be seen in FIG. 6, the expression of the AFP gene and the HNF4α gene was observed in the positive control, whereas the expression of the AFP gene and the HNF4α gene was not observed in the negative control. The expression of the AFP gene and the HNF4α gene was observed in all the samples according to the present example. These results demonstrate that, by inhibiting ROCK activity, liver cells can be produced from dispersed pluripotent cells and pluripotent cells forming cell clusters with high differentiation efficiency.

Example 4

The present example was conducted to demonstrate that mature liver cells can be produced from pluripotent cells by inhibiting ROCK activity and that mature liver cells having properties closer to those of mature liver cells in vivo can be induced by using a plate coated with an extracellular matrix protein-containing coating.

(1) Production of Scaffold-coated Plate

A plate coated with a blood component-containing coating was produced in the following manner. First, 0.1% (vol %) gelatin solution was added to the 24-well plate. Then, the 24-well plate was allowed to stand still at 37° C. for 30 minutes. The gelatin solution was removed, and a serum-containing culture solution was added. Then, the 24-well plate was incubated at 37° C. for at least 24 hours. The serum-containing culture solution had the composition shown in Table 2 below. On the other hand, a plate coated with an extracellular matrix protein-containing coating was produced in the following manner. First, 80 µl of Matrigel™ (BD Biosciences) and 6 ml of DMEM/F12 (SIGMA-Ardrich) were mixed together to prepare a Matrigel solution. The Matrigel solution was added to the 24-well plate, and the 24-well plate was incubated at 4° C. for at least 24 hours.

TABLE 2

| | |
|---|---:|
| DMEM/F12 (SIGMA-Ardrich) | 450 ml |
| Fetal bovine serum (CCB) | 50 ml |
| Glutamine solution (GIBCO) | 5 ml |
| Penicillin/streptomycin solution (Wako) | 5 ml |
| 14.3 mol/l β-mercaptoethanol (SIGMA-Ardrich) | 3.5 µL |
| Total | about 510 ml |

(2) Production of Liver Cells

Pluripotent cells were differentiated into liver cells in the same manner as in (1) in Example 1 and (2) in Example 3, except that, instead of the 24-well plate, the plate coated with the blood component-containing coating or the plate coated with the extracellular matrix protein-containing coating was used.

(3) Production of Mature Liver Cells (Culture Day 13 and Later)

The culture solution used on culture day 12 was removed, and a liver cell culture solution (a liver cell mature culture solution, hepatocyte basal medium, LONZA) containing 30 ng/ml OSM (R&D Systems) and 50 ng/ml human HGF (PEPROTECH) was added. Then, the cells were cultured for 21 days under the above-described culture conditions. During the culture for 21 days, the culture solution in the wells was replaced every 2 days with a fresh culture solution having the same composition.

(4) Expression of Mature Liver Cell Marker

The culture solution used on culture day 33 was removed, and the wells were washed with phosphate buffered saline (PBS). Then, 4% formaldehyde was added to the wells, and the cells were immobilized at 24° C. for 5 minutes. Thereafter, the wells were washed with PBS again, and a trans-cellular fluid was added thereto to perform cell membrane permeabilization at 4° C. for at least 24 hours. As the transcellular fluid, PBS containing 0.5% (vol %) Triton X-100 (Sigma-Aldrich) was used. After the cell permeabilization, the cells were reacted with a rabbit anti-human A1AT polyclonal antibody (DAKO). Further, an Alexa Fluor® 488 labeled anti-rabbit IgG antibody was added to the wells to stain the cells. Then, nuclear staining was performed using DAPI (Life Technologies). After the staining, the wells were observed using a fluorescence microscope (Nikon Eclipse Ti-E, NIKON CORPORATION).

Figure 7:
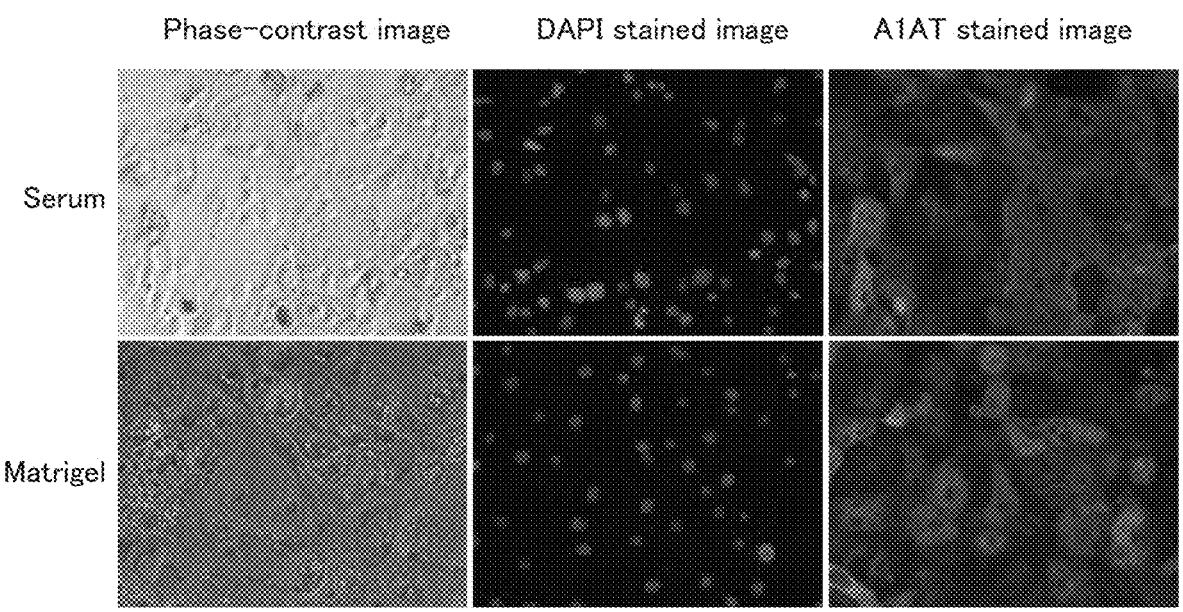
FIG. 7 shows photographs indicating the expression of A1AT in Example 4.

The results obtained are shown in FIG. 7. FIG. 7 shows photographs indicating the expression of A1AT. In FIG. 7, the photographs in the upper row show the results obtained when the plate coated with the blood component-containing coating was used, and the photographs in the lower row show the results obtained when the plate coated with the extracellular matrix protein-containing coating was used. In FIG. 7, the photographs show, from the left, phase-contrast images, DAPI stained images, and A1AT stained images. As can be seen in the phase-contrast images in FIG. 7, when either of the plates coated with the above scaffolds was used, the cells became larger and swelling of the colonies was observed, so that it was determined that the cells were mature liver cells. Also, when either of the plates coated with the above scaffolds was used, A1AT was expressed strongly. These results demonstrate that mature liver cells can be produced from pluripotent cells by inhibiting ROCK activity.

(5) Expression of Mature Liver Cell Marker

Regarding the A1AT stained images in FIG. 7, the A1AT staining intensity was measured using software (CellProfiler, Broad Institute).

Figure 8:
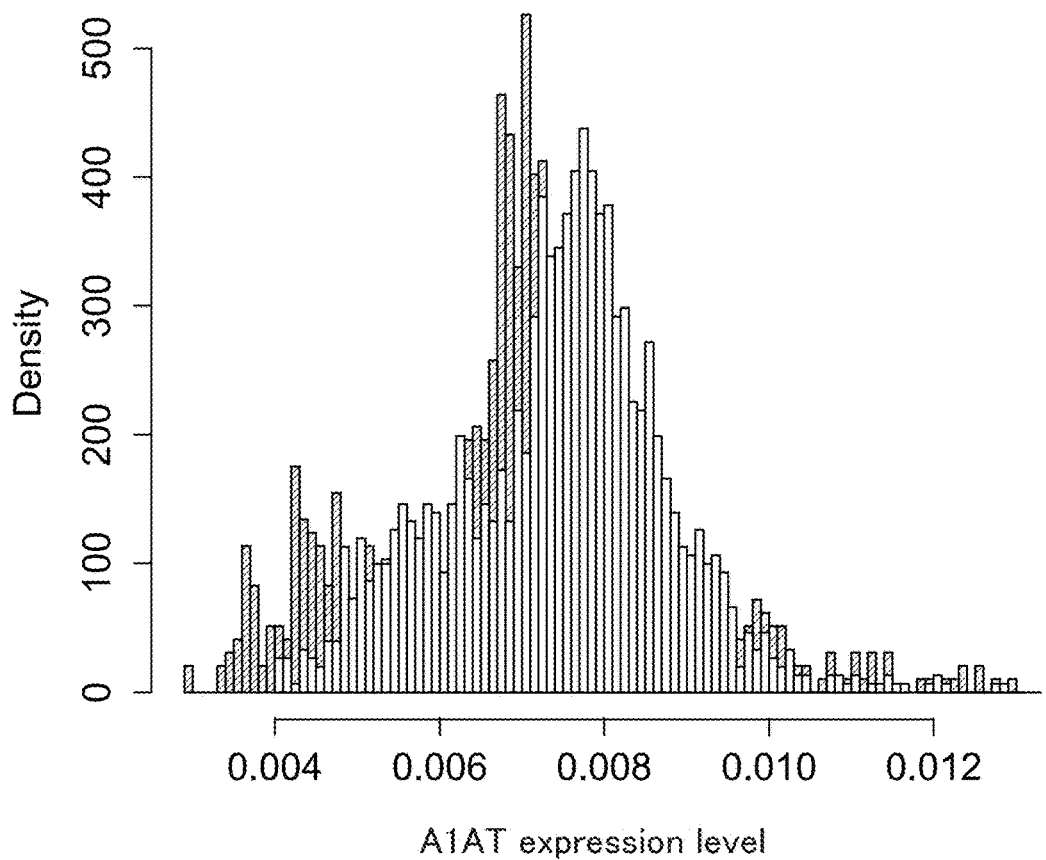
FIG. 8 is a histogram showing the expression level of A1AT in Example 4.

The results obtained are shown in FIG. 8. FIG. 8 is a histogram showing the expression level of A1AT. In FIG. 8, the horizontal axis indicates the expression level of A1AT, and the vertical axis indicates the number of the cells. In FIG. 8, the hatched bars show the results obtained when the plate coated with the blood component-containing coating was used, and open bars show the results obtained when the plate coated with the extracellular matrix protein-containing coating was used. As can be seen in FIG. 8, the A1AT expression level observed when the plate coated with the extracellular matrix protein-containing coating was used was higher than the A1AT expression level observed when the plate coated with the blood component-containing coating was used. These results demonstrate that mature liver cells having properties closer to those of mature liver cells in vivo can be induced by using a plate coated with an extracellular matrix protein-containing coating.

Example 5

The present example was conducted to demonstrate that mature liver cells produced from pluripotent cells by inhibiting ROCK activity have the function of mature liver cells.

(1) Production of Mature Liver Cells

Mature liver cells were produced in the same manner as in (1) to (3) in Example 4, except that the cells were cultured for 28 days in (3) in Example 4. Also, mature liver cells were produced in the same manner, except that the plate coated with the extracellular matrix protein-containing coating was used in addition to the plate coated with the blood component-containing coating.

(2) Examination of Mature Liver Cell Function

An indocyanine green (ICG) solution (Sigma-Aldrich) was added to the wells at a concentration of 1 mg/ml. Then, the cells were cultured for 1 hour under the above-described culture conditions, thereby causing the ICG to be taken into the resultant mature liver cells. Next, the wells were washed with the culture solution used on culture day 12, and the culture solution was added. Then, the ICG was released by culturing the cells for 12 hours under the above-described culture conditions.

Figure 9:
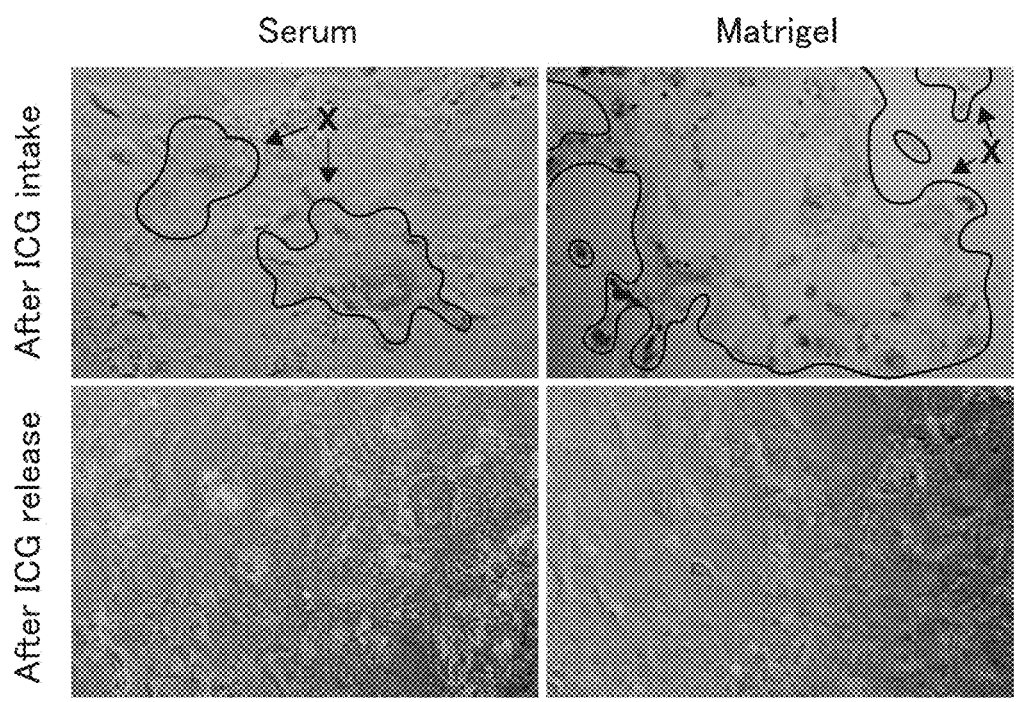
FIG. 9 shows photographs indicating uptake and release of indocyanine green (ICG) in Example 5.

The results obtained are shown in FIG. 9. FIG. 9 shows photographs indicating uptake and release of the ICG. In FIG. 9, the photographs in the upper row show the results obtained after the uptake of the ICG, and the photographs in the lower row show the results obtained after the release of the ICG. In FIG. 9, the photographs on the left show the results obtained when the plate coated with the blood component-containing coating was used, and the photographs on the right show the results obtained when the plate coated with the extracellular matrix protein-containing coating was used. As indicated with the arrows X in the photographs in the upper row in FIG. 9, when either of the plates coated with the above scaffolds was used, the uptake of the ICG was observed. Also, as can be seen in the photographs in the lower row in FIG. 9, when either of the plates coated with the above scaffolds was used, the release of the ICG was observed. Also, the efficiency of the ICG uptake when the plate coated with the extracellular matrix protein-containing coating was used was higher than the efficiency of the ICG uptake when the plate coated with the blood component-containing coating was used. These results demonstrate that mature liver cells produced from pluripotent cells by inhibiting ROCK activity have the function of mature liver cells. These results also demonstrate that mature liver cell having properties closer to those of mature liver cells in vivo can be induced by using a plate coated with an extracellular matrix protein-containing.

Example 6

The present example was conducted to demonstrate that mature liver cells can be produced from pluripotent cells by inhibiting ROCK activity.

(1) Production of Mature Liver Cells

Mature liver cells were produced in the same manner as in (1) to (3) in Example 4, except that the cells were cultured for 20 days in (3) in Example 4.

(2) Expression of Mature Liver Cell Markers

After the culture on culture day 32, the cells were collected from each well. Then, cDNA was synthesized in the same manner as in (4) in Example 2, except that the collected cells were used instead of the endodermal cells. Thereafter, PCR was performed in the same manner as in (2) in Example 3, thereby amplifying the CYP1A1 gene, the CYP2C9 gene, the CYP2C19 gene, the MRP2 gene, the MDR/TAP gene, the UGT1A1 gene, the A1AT gene, the TDO2 gene, the HNF4α gene, and the GAPDH gene in the RNA. The PCR solution after the amplification was applied to electrophoresis using 1.8% agarose gel. After the electrophoresis, the gel was stained with Gel Red™, and the expression of the CYP1A1 gene, the CYP2C9 gene, the CYP2C19 gene, the MRP2 gene, the MDR/TAP gene, the UGT1A1 gene, the A1AT gene, the TDO2 gene, the HNF4α gene, and the GAPDH gene was examined. In the PCR, the following primer sets were used for the amplification of the CYP1A1 gene, the CYP2C9 gene, the CYP2C19 gene, the MRP2 gene, the MDR/TAP gene, the UGT1A1 gene, the A1AT gene, and the TDO2 gene, respectively, and the primer sets used in (3) in Example 3 and (4) in Example 2 were used for the amplification of the HNF4α gene and the GAPDH gene, respectively. The expression of the CYP1A1 gene, the CYP2C9 gene, the CYP2C19 gene, the MRP2 gene, the MDR/TAP gene, the UGT1A1 gene, the A1AT gene, the TDO2 gene, the HNF4α gene, and the GAPDH gene was examined in the same manner, except that: as a positive control, human liver homogenate (obtained from Clontech) was used instead of the collected cells; as a negative control, the cDNA was not added; as control 1, a H9 cell line was used instead of the collected cells; and as control 2, HepG2 cells were used instead of the collected cells.

Primer Set for CYP1A1 Gene Amplification (SEQ ID NO: 9)
5'-ACCTGAATGAGAAGTTCTACAGC-3'

(SEQ ID NO: 10)
5'-CTGGGGTTCATCACCAAATACA-3'

Primer Set for CYP2C9 Gene Amplification (SEQ ID NO: 11)
5'-CCCTGGATCCAGATCTGCAA-3'

(SEQ ID NO: 12)
5'-TGCTTGTCGTCTCTGTCCCA-3'

Primer Set for CYP2C19 Gene Amplification (SEQ ID NO: 13)
5'-GGTGCTGCATGGATATGAAGTG-3'

(SEQ ID NO: 14)
5'-TGGATCCAGGGGGTGCTTAC-3'

Primer Set for MRP2 Gene Amplification (SEQ ID NO: 15)
5'-ACCTCCAACAGGTGGCTTGCA-3'

(SEQ ID NO: 16)
5'-ACACCAATCTTCTCCATGCTACC-3'

Primer Set for MDR/TAP Gene Amplification (SEQ ID NO: 17)
5'-GTGCTGAGTAAGATTCAGCATGGG-3'

(SEQ ID NO: 18)
5'-AGCATGTCATCTTCAGTTGCATCCT-3'

Primer Set for UGT1A1 Gene Amplification (SEQ ID NO: 19)
5'-GTGCCTTTATCACCCATGCT-3'

(SEQ ID NO: 20)
5'-TCTTGGATTTGTGGGCTTTC-3'

Primer Set for A1AT Gene Amplification (SEQ ID NO: 21)
5'-ACATTTACCCAAACTGTCCATT-3'

(SEQ ID NO: 22)
5'-GCTTCAGTCCCTTTCTCGTC-3'

Primer Set for TDO2 Gene Amplification (SEQ ID NO: 23)
5'-GACGGCTGTCATACAGAGCA-3'

(SEQ ID NO: 24)
5'-CGCAGGTAGTGATAGCCTGA-3'

Figure 10:
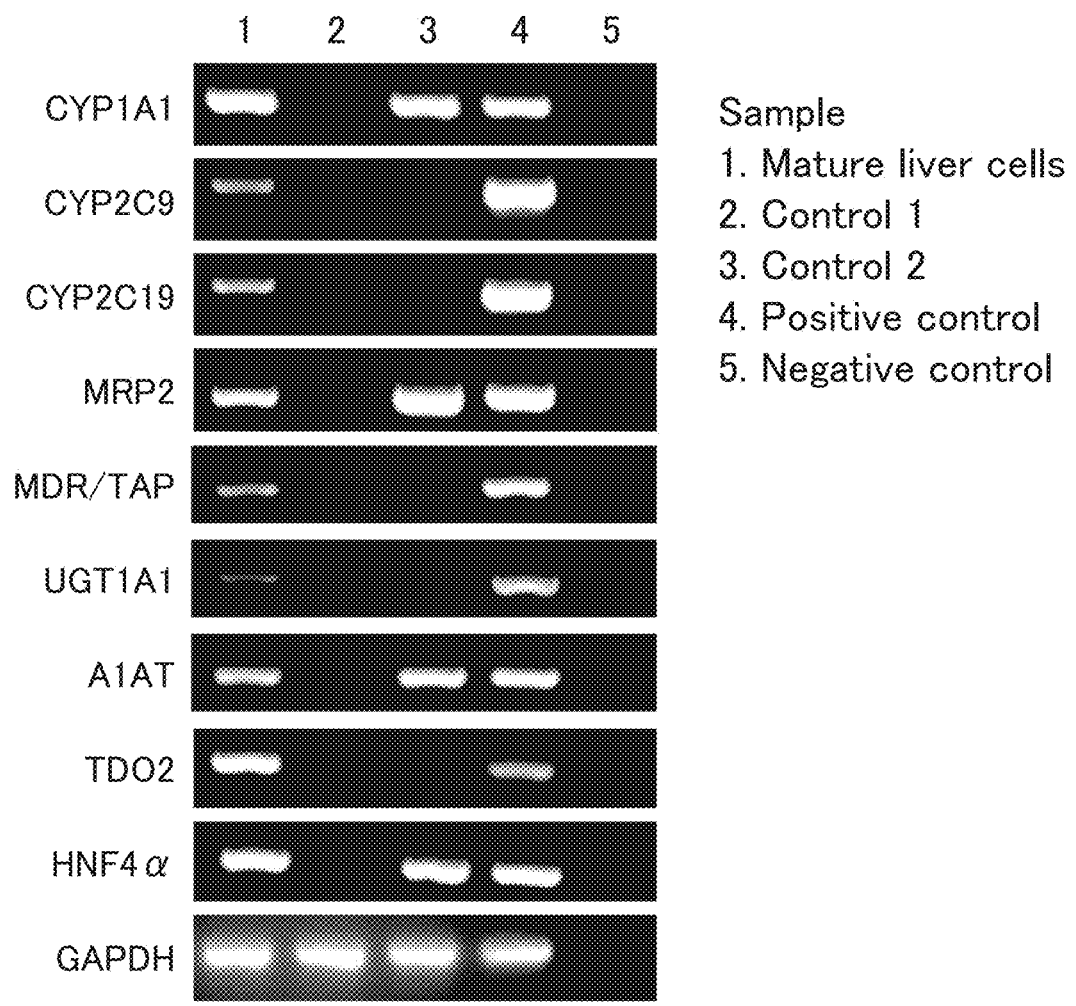
FIG. 10 shows photographs indicating the expression of the CYP1A1 gene, the CYP2C9 gene, the CYP2C19 gene, the MRP2 gene, the MDR/TAP gene, the UGT1A1 gene, the A1AT gene, the TDO2 gene, the HNF4α gene, and the GAPDH gene in Example 6.

The results obtained are shown in FIG. 10. FIG. 10 shows photographs indicating the expression of the CYP1A1 gene, the CYP2C9 gene, the CYP2C19 gene, the MRP2 gene, the MDR/TAP gene, the UGT1A1 gene, the A1AT gene, the TDO2 gene, the HNF4α gene, and the GAPDH gene. In FIG. 10, the lane numbers are indicated above the photographs, the type of the gene is indicated on the left of each photograph, and the respective lanes indicate, from the left, the results obtained regarding the mature liver cells produced in the present example, control 1, control 2, the positive control, and the negative control. As can be seen in FIG. 10, all the genes were expressed in the positive control, and none of the genes were expressed in the negative control. The mature liver cells produced in the present example expressed all the genes. These results demonstrate that mature liver cells having properties closer to those of mature liver cells in vivo can be produced by inhibiting ROCK activity.

Example 7

The present example was conducted to demonstrate that mature liver cells can be obtained by maturing, in a microfluidic device, liver cells that have been produced from pluripotent cells by inhibiting ROCK activity and that the obtained mature liver cells have the function of mature liver cells.

(1) Production of Device

Using 3D computer graphics software (3D-CAD, Auto-CAD, Blender), a mask with a template design for the structure of the microfluidic device of FIG. 1 was produced. Cell culture chambers of the device each had a length of 9000 μm, a width of 1500 μm, and a height of 200 μm. The openings of the device each had a diameter of 1000 μm and a height of 5000 μm. The device was stored in a desiccator before use. Next, the template design was converted to a file in the stl format. The stl file obtained by the conversion was transferred to a 3D printer (AGILISTA, Keyence), and the template was printed.

A silicone elastomer base and a curing agent (SYL-GARD® 184 Silicone Elastomer kit [base, curing agent], Dow corning) were mixed together at a weight ratio of 10:1 using a stirring mixer to produce a PDMS mixed solution. The PDMS mixed solution was poured into the template. Thereafter, the template was deaerated for 30 minutes in a desiccator. After deaeration, the template was heated overnight in an oven at 65° C. Then, PDMS formed in the template was collected.

An OmniTray (NuncOmniTray, Thermo scientific) or a glass bottom dish (Iwaki Glass Co., Ltd.) was subjected to a corona treatment using a Corona Fit CFG-500 (Shinko Electric & Instrumentation Co., Ltd.). The surface of the PDMS also was subjected to a corona treatment in the same manner. Next, the OmniTray or the glass bottom dish after the corona treatment was bonded to the PDMS. This was then heated overnight in an oven at 65° C. Thus, the device shown in FIG. 1 was produced.

(2) Production of Liver Cells

Liver cells were prepared in the same manner as in (1) and (2) in Example 3, except that the H9 cell line was seeded at a cell density of $1 \times 10^5$ cells/well. The thus-obtained liver cells were collected using PBS containing TrypLE™ Express.

(3) Production of Mature Liver Cells

10 μl of the serum-containing culture solution or the Matrigel solution was introduced into the device, and the device was incubated at 4° C. for at least 24 hours. Next, the liver cell mature culture solution was introduced into the device to wash flow paths of the device. Further, the collected liver cells were introduced to the device so as to achieve a cell density of $5 \times 10^4$ cells/device or $1 \times 10^5$ cells/device. Thereafter, the liver cells introduced to the device were cultured for 3 hours to cause the introduced liver cells to adhere to the cell culture chambers. The culture conditions were set as follows: 37° C. and 5% $CO_2$. As the culture solution, the above-described liver cell mature culture solution was used. After the culture, the liver cell mature culture solution was introduced to remove the liver cells that had not adhered to the cell culture chambers. Then, mature liver cells were produced in the same manner as in (3) in Example 4, except that the liver cell mature culture solution was replaced daily.

(4) Expression of Mature Liver Cell Marker

The culture solution used on culture day 33 was removed. Thereafter, the expression of the mature liver cell marker was observed using a fluorescence microscope in the same manner as in (4) in Example 4.

Figure 11:
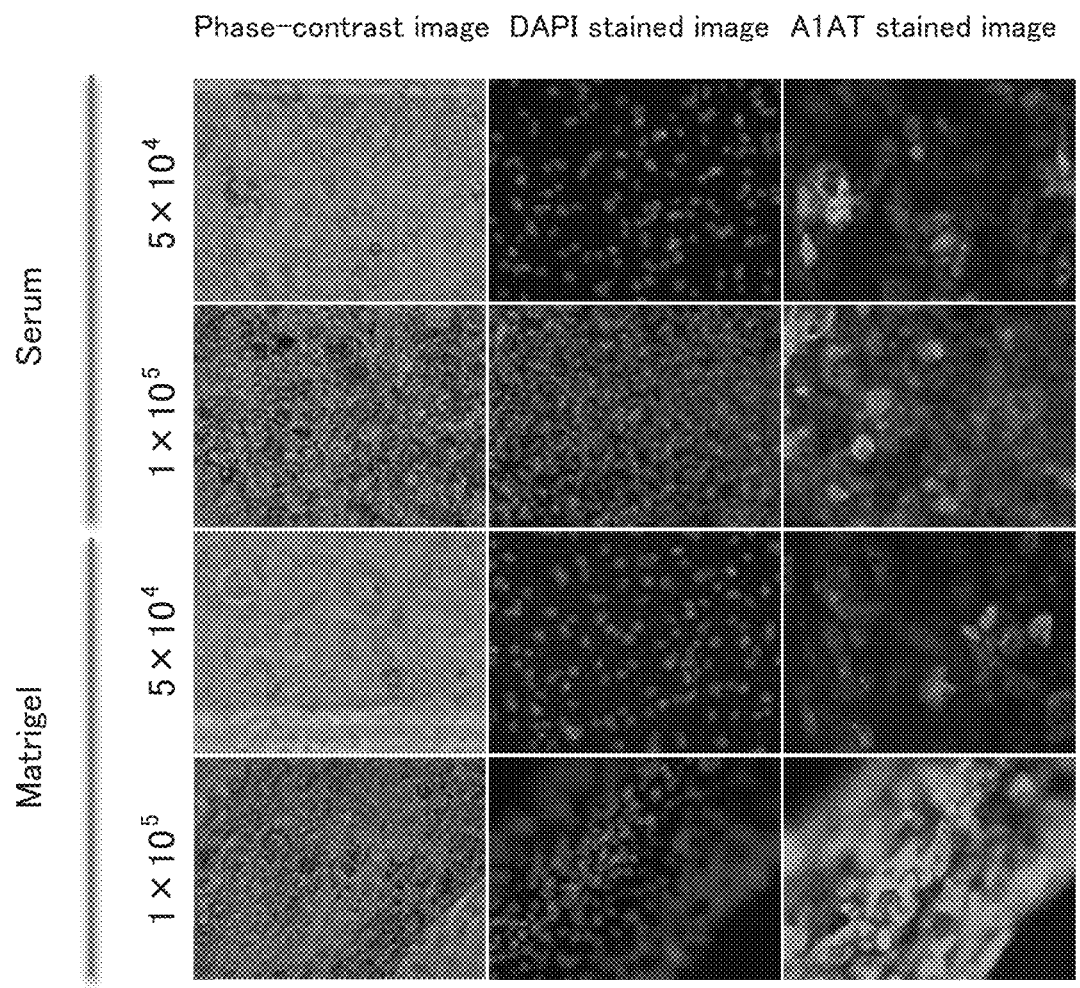
FIG. 11 shows photographs indicating the expression of A1AT in Example 7.

The results obtained are shown in FIG. 11. FIG. 11 shows photographs indicating the expression of A1AT. In FIG. 11, the photographs in the first row show the results obtained when the plate coated with the blood component-containing coating was used and the liver cells were seeded at the cell density of $5 \times 10^4$ cells/device. The photographs in the second row show the results obtained when the plate coated with the blood component-containing coating was used and the liver cells were seeded at the cell density of $1 \times 10^5$ cells/device. The photographs in the third row show the results obtained when the plate coated with the extracellular matrix protein-containing coating was used and the liver cells were seeded at the cell density of $5 \times 10^4$ cells/device. The photographs in the fourth row show the results obtained when the plate coated with the extracellular matrix protein-containing coating was used and the liver cells were seeded at the cell density of $1 \times 10^5$ cells/device. The photographs in FIG. 11 show, from the left, phase-contrast images, DAPI stained images, and A1AT stained images. As can be seen in the phase-contrast images in FIG. 11, when either of the plates coated with the above scaffolds was used, the cells became larger and swelling of the colonies was observed, so that it was determined that the cells were mature liver cells. Also, as can be seen in the photographs in the fourth row in FIG. 11, it was found that, when the plate coated with the extracellular matrix protein-containing coating was used and the liver cells were seeded at the cell density of $1 \times 10^5$ cells/device, the mature liver cells formed a three-dimensional structure. These results demonstrate that mature liver cells can be obtained by maturing, in a microfluidic device, liver cells that have been produced from pluripotent cells by inhibiting ROCK activity. These results also demonstrate that three-dimensional mature liver cells are obtained when the microfluidic device is used and the cell density of the liver cells at the start of the maturation is set high (specifically, $1 \times 10^3$ to $1 \times 10^5$ cells/cm$^2$, more preferably $1 \times 10^4$ to $5 \times 10^4$ cells/cm$^2$).

(5) Examination of Mature Liver Cell Function

Mature liver cells were produced in the same manner as in (1) to (3) in Example 7, except that the plate coated with the extracellular matrix protein-containing coating used in (4) in Example 7 was used and the liver cells were seeded at a cell density of $1 \times 10^5$ cells/device. Next, the ICG solution was added to the device at a concentration of 1 mg/ml. Then, the cells were cultured for 1 hour under the above-described culture conditions, thereby causing the ICG to be taken into the resultant mature liver cells. After washing with the liver cell mature culture solution, the liver cell mature culture solution was added again. Then, the ICG was released by culturing the cells for 12 hours under the above-described culture conditions.

Figure 12:
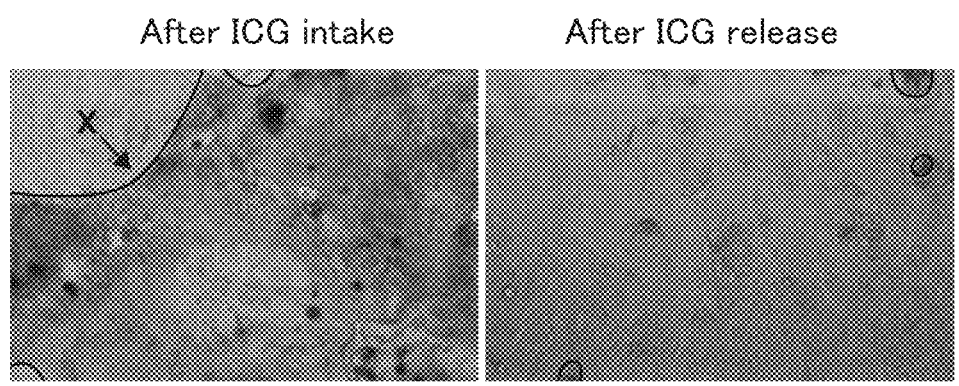
FIG. 12 shows photographs indicating uptake and release of ICG in Example 7.

The results obtained are shown in FIG. 12. FIG. 12 shows photographs indicating uptake and release of the ICG. In FIG. 12, the left photograph shows the result obtained after the uptake of the ICG, and the right photograph shows the result obtained after the release of the ICG. In the left photograph of FIG. 12, the uptake of the ICG was observed as indicated with the arrow X. Also, as can be seen in the right photograph of FIG. 12, the release of the ICG was observed. These results demonstrate that mature liver cells matured in a microfluidic device have the function of mature liver cells.

Example 8

The present example was conducted to demonstrate that endodermal cells can be produced from pluripotent cells with very high differentiation efficiency by inhibiting ROCK activity.

Differentiation into endodermal cells was induced 20 times in total in the same manner as in (1) in Example 1. Then, on culture day 5, whether differentiation into endodermal cells was induced was examined. As a control, differentiation into endodermal cells was induced 25 times in total in the same manner, except that the ROCK activity inhibitory compound was not added. Then, on culture day 5, whether differentiation into endodermal cells was induced was examined.

The results obtained are shown in Table 3. As can be seen in Table 3, the probability of endodermal cell induction in the present example was 100%. In contrast, the probability of endodermal cell induction in the control was 8%. These results demonstrate that endodermal cells can be produced from pluripotent cells with very high differentiation efficiency by inhibiting ROCK activity.

TABLE 3

| | Number of times endodermal cell induction was performed (probability of induction) |
|---|---|
| Example | 20/20 times (100%) |
| Control | 2/25 times (8%) |

Example 9

The present example was conducted to demonstrate that mature liver cells can be produced from pluripotent cells in a shorter period by inhibiting ROCK activity.

(1) Production of Liver Cells and Mature Liver Cells

Liver cells and mature liver cells were produced in the same manner as in (1) to (3) in Example 4, except that the plate coated with the extracellular matrix protein-containing coating was used. Then, the cells were collected on culture day 20, culture day 25, culture day 30, and culture day 35. Then, cDNA was synthesized in the same manner as in (4) in Example 2, except that the collected cells were used instead of the endodermal cells. Thereafter, with the thus-obtained cDNA as a template, PCR was performed using the PCR reagent and a thermal cycler (Mastercycler® pro, Eppendorf AG) in accordance with the protocols attached thereto, thereby amplifying the ALB gene, the CYP2C19 gene, the A1AT gene, the MDR/TAP gene, and the GAPDH gene in the RNA. The PCR solution after the amplification was applied to electrophoresis using 1.8% agarose gel. After the electrophoresis, the gel was stained with Gel Red™, and the expression of the ALB gene, the CYP2C19 gene, the A1AT gene, the MDR/TAP gene and the GAPDH gene was examined. In the PCR, the following primer set was used for the amplification of the ALB gene, the primer set used in (4) in Example 2 was used for the amplification of the GAPDH gene, and the primer sets used in (2) in Example 6 were used for the amplification of the CYP2C19 gene, the A1AT gene, and the MDR/TAP gene. The expression of the ALB gene, the CYP2C19 gene, the A1AT gene, the MDR/TAP gene, and the GAPDH gene was examined in the same manner, except that: as a positive control, the human liver homogenate was used instead of the collected cells; as a negative control, the cDNA was not added; as control 1, a H9 cell line was used instead of the collected cells; and as control 2, HepG2 cells were used instead of the collected cells.

Primer Set for ALB Gene Amplification

```
                                         (SEQ ID NO: 25)
5'-TTGGCACAATGAAGTGGGTA-3'

(SEQ ID NO: 26)
5'-AAAGGCAATCAACACCAAGG-3'
```

Figure 13:
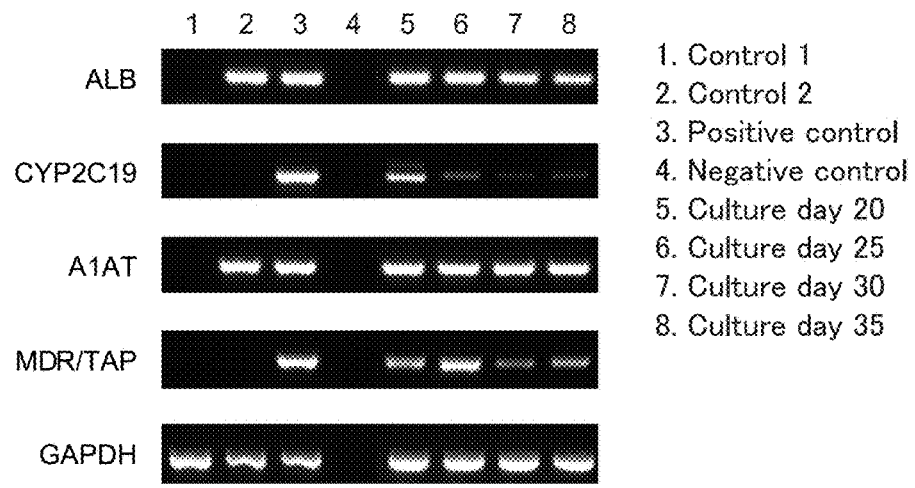
FIG. 13 shows photographs indicating the expression of the ALB gene, the CYP2C19 gene, the A1AT gene, the MDR/TAP gene, and the GAPDH gene in Example 9.

The results obtained are shown in FIG. 13. FIG. 13 shows photographs indicating the expression of the ALB gene, the CYP2C19 gene, the A1AT gene, the MDR/TAP gene, and the GAPDH gene. In FIG. 13, the types of the samples are indicated above the photographs, the type of the gene is indicated on the left of each photograph, and the respective lanes indicate, from the left, the results obtained regarding control 1, control 2, the positive control, the negative control, the sample on culture day 20, the sample on culture day 25, the sample on culture day 30, and the sample on culture day 35. As can be seen in FIG. 13, all the genes were expressed in the positive control, and none of the genes were expressed in the negative control. The samples on culture day 20 to culture day 35 expressed all the genes. These results demonstrate that, by inhibiting the ROCK activity, differentiation into mature liver cells having properties closer to those of mature liver cells in vivo can be induced even on culture day 20. That is, while the method disclosed in Non-Patent Document 1 requires 35 days of culture, the endodermal cell production method of the present invention can produce endodermal cells capable of differentiating into mature liver cells in a shorter period.

Example 10

The present example was conducted to demonstrate that pancreatic cells can be produced from dispersed pluripotent cells by inhibiting ROCK activity.

(1) Production of Endodermal Cells

Endodermal cells were produced in the same manner as culture day 1 to culture day 4 in (1) in Example 1, except that a Nunc™ 4-well dish (Thermo Scientific) was used instead of the 24-well dish and that induced pluripotent stem cells (253G1 hiPSCs, provided by Yamanaka Lab, the Center for iPS Cell Research and Application, Kyoto University) were used instead of the H9 cell line. The 4-well dish was coated by adding a DMEM/F12 culture solution containing 10 (v/v) % fetal bovine serum to the dish and then allowing the dish to stand still at 37° C. for at least 24 hours.

(2) Production of Pancreatic Cells (Culture Day 5 to Culture Day 7)

The culture solution used on culture day 4 was removed, and an iMEM/B-27 culture solution containing 100 µg/ml KGF (R&D systems) was added. Then, the cells were cultured for 3 days under the above-described culture conditions. The iMEM/B-27 culture solution had the composition shown in Table 4 below. During the culture for 3 days, the culture solution in the wells was replaced daily with a fresh culture solution having the same composition.

TABLE 4

| | |
|---|---|
| Modified IMEM no gentamicin (Gibco) | 99 ml |
| B-27 ® supplement, XenoFree CTS ™ (Gibco) | 1 ml |
| Penicillin/streptomycin solution (Wako) | 1 ml |
| Total | 101 ml |

(Culture Day 8 to Culture Day 10)

The culture solution used on culture day 7 was removed, and an iMEM/B-27 culture solution containing 1 mmol/l KAAD-CYC (Toronto Research Chemicals Inc.), 10 µmol/l TTNPB (Tocris), and 100 µg/ml Noggin was added. Then, the cells were cultured for 3 days under the above-described culture conditions. During the culture for 3 days, the culture solution in the wells was replaced daily with a fresh culture solution having the same composition.

(Culture Day 11 to Culture Day 16)

The culture solution used on culture day 10 was removed. Thereafter, PBS containing 0.25% trypsin and 0.48 mmol/l EDTA was added, and the cells were treated for 3 minutes. After the treatment, the cells were collected and centrifuged, and the supernatant was removed. An iMEM/B-27 culture solution containing 10 µmol/l Y27632, 100 µg/ml KGF, 100 µg/ml Noggin and 500 µg/ml EGF (R&D systems) was further added to suspend the cells. Thereafter, the cells were seeded to the 4-well dish at a cell density of $2 \times 10^5$ cells/well, and the cells were cultured for 6 days under the above-described culture conditions. During the culture for 6 days, the culture solution in the wells was replaced daily with a fresh culture solution having the same composition.

(3) Expression of Pancreatic Cell Marker Proteins

The culture solution used on culture day 16 was removed, and the wells were washed with PBS. Then, 4% formaldehyde was added to the wells, and the cells were immobilized at 24° C. for 5 minutes. Thereafter, the wells were washed with PBS again, and a transcellular fluid was added thereto to perform cell membrane permeabilization at 4° C. for at least 24 hours. As the transcellular fluid, PBS containing 0.5% (vol %) Triton X-100 was used. After the cell permeabilization, the cells were reacted with a rabbit anti-human NKX6.1 polyclonal antibody (R&D systems) or a rabbit anti-human insulin polyclonal antibody (Abcam). Further, an Alexa Fluor® 488 labeled anti-rabbit IgG antibody was added to the wells to stain the cells. Then, nuclear staining was performed using DAPI. After the staining, the wells were observed using the fluorescence microscope.

Figure 14:
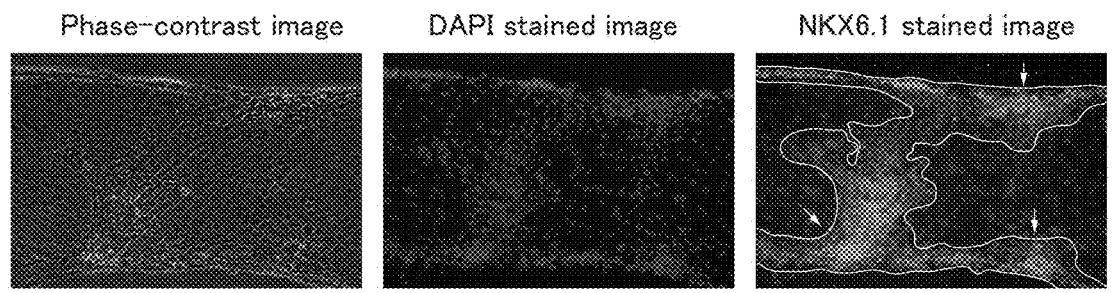
FIG. 14 shows photographs indicating the expression of NKX6.1 and insulin in Example 10.
Figure 14:
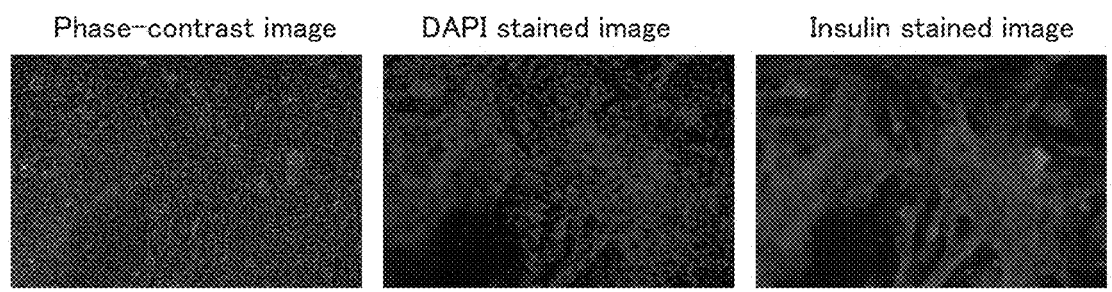

The results obtained are shown in FIG. 14. In FIG. 14, (A) shows photographs indicating the expression of NKX6.1, and (B) shows photographs indicating the expression of insulin. In (A) of FIG. 14, the photographs show, from the left, a phase-contrast image, a DAPI stained image, and an NKX6.1 stained image. In (B) of FIG. 14, the photographs show, from the left, a phase-contrast image, a DAPI stained image, and an insulin stained image. As can be seen in (A) and (B) of FIG. 14, the pancreatic cells on culture day 16 expressed NKX6.1 and insulin, which are pancreatic cell markers. These results demonstrate that pancreatic cells can be produced from dispersed pluripotent cells by inhibiting the ROCK activity.

(4) Expression of Pancreatic Cell Marker Genes

After the culture on culture day 16, the cells were collected from each well. Then, cDNA was synthesized in the same manner as in (4) in Example 2, except that the collected cells were used instead of the endodermal cells. Thereafter, the expression of the PTF1α gene, the NKX6.1 gene, the PDX1 gene, and the GAPDH gene was examined in the same manner as in (3) in Example 3, except that the following primer sets were used for amplification of the PTF1α gene, the NKX6.1 gene, and the PDX1 gene.

Primer Set for PTF1α Gene Amplification

```
                                        (SEQ ID NO: 27)
    5'-CCCCAGCGACCCTGATTA-3'

(SEQ ID NO: 28)
    5'-GGACACAAACTCAAATGGTGG-3'
```

Primer Set for NKX6.1 Gene Amplification

```
                                        (SEQ ID NO: 29)
    5'-ATTCGTTGGGGATGACAGAG-3'

(SEQ ID NO: 30)
    5'-TGGGATCCAGAGGCTTATTG-3'
```

Primer Set for PDX1 Gene Amplification

```
                                        (SEQ ID NO: 31)
    5'-AGCAGTGCAAGAGTCCCTGT-3'

(SEQ ID NO: 32)
    5'-CACAGCCTCTACCTCGGAAC-3'
```

Figure 15:
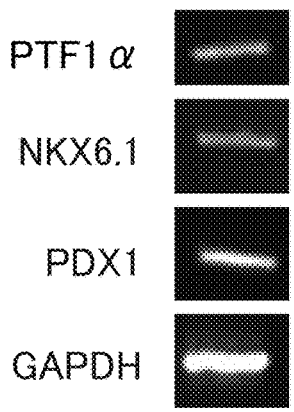
FIG. 15 shows photographs indicating the expression of the PTF1α gene, the NKX6.1 gene, the PDX1 gene, and the GAPDH gene in Example 10.

The results obtained are shown in FIG. 15. FIG. 15 shows photographs indicating the expression of the PTF1α gene, the NKX6.1 gene, the PDX1 gene, and the GAPDH gene. In FIG. 15, the type of the gene is indicated on the left of each photograph. As can be seen in FIG. 15, the pancreatic cells on culture day 16 expressed the PTF1α gene, the NKX6.1 gene, and the PDX1 gene, which are pancreatic cell markers. These results demonstrate that the pancreatic cells can be produced from dispersed pluripotent cells by inhibiting the ROCK activity.

While the present invention has been described above with reference to illustrative embodiments and examples, the present invention is by no means limited thereto. Various changes and modifications that may become apparent to those skilled in the art may be made in the configuration and specifics of the present invention without departing from the scope of the present invention.

This application claims priority from Japanese Patent Application No. 2014-261088 filed on Dec. 24, 2014. The entire disclosure of this Japanese patent application is incorporated herein by reference.

INDUSTRIAL APPLICABILITY

As specifically described above, the endodermal cell production method of the present invention can induce differentiation of pluripotent cells into endodermal cells even when the pluripotent cells are dispersed and can achieve improved endodermal cell production efficiency. Accordingly, the present invention is very useful in the fields of clinical practice (such as regenerative medicine), medical, life science, etc.

EXPLANATION OF REFERENCE NUMERALS

1: cell culture chamber
2: opening
100: device

Sequence Listing 2015.12.10_TF14087WO_ST25.txt

The invention claimed is:

1. A method for producing endodermal cells by inducing differentiation of pluripotent cells into the endodermal cells, the method comprising the step of:
    inducing differentiation of the pluripotent cells into the endodermal cells in the presence of an endodermal cell inducing factor,
    wherein, in the inducing step, ROCK protein activity is inhibited, and
    the endodermal cell inducing factor comprises a PI$_3$K protein activity inhibitor.

2. The endodermal cell production method according to claim 1, wherein
    in the inducing step, a cell density of the pluripotent cells at the start of the induction is from $0.5 \times 10^4$ to $2 \times 10^5$ cells/cm$^2$.

3. The endodermal cell production method according to claim 1, wherein
    the pluripotent cells are dispersed.

4. The endodermal cell production method according to claim 1, wherein
    the endodermal cell inducing factor comprises at least one selected from the group consisting of a TGF-β family protein, bFGF, a GSK-3β protein activity inhibitor, and an mTOR protein activity inhibitor.

5. The endodermal cell production method according to claim 4, wherein
    the TGF-β family protein comprises at least one selected from the group consisting of activin, BMP-4, and NODAL.

6. The endodermal cell production method according to claim 1, wherein
    the inducing step is a step of inducing differentiation of the pluripotent cells into the endodermal cells in the presence of a pluripotent cell culture solution containing the endodermal cell inducing factor.

7. The endodermal cell production method according to claim 6, wherein
    the pluripotent cell culture solution contains a TGF-β family protein, bFGF, and insulin.

8. The endodermal cell production method according to claim 1, wherein
    in the inducing step, the ROCK protein activity is inhibited by a ROCK protein activity inhibitory compound.

9. A liver cell production method comprising the step of:
    differentiating endodermal cells into liver cells in the presence of a liver cell differentiation factor,
    wherein the endodermal cells are obtained by the endodermal cell production method according to claim 1.

10. The liver cell production method according to claim 9, wherein
    the liver cell differentiation factor comprises at least one selected from the group consisting of a TGF-β family protein, FGF10, and WNT.

11. The liver cell production method according to claim 10, wherein
    the TGF-β family protein comprises at least one selected from the group consisting of activin, BMP-4, and NODAL.

12. The liver cell production method according to claim 9, further comprising the step of:
    maturing the liver cells in the presence of a liver cell maturation factor.

13. The liver cell production method according to claim 12, wherein
    in the maturing step, the liver cells are matured on a scaffold.

14. The liver cell production method according to claim 13, wherein
the scaffold is a coating containing an extracellular matrix protein, a coating containing a blood component or a coating containing a recombinant protein.

15. The liver cell production method according to claim 12, wherein
the liver cell maturation factor comprises at least one selected from the group consisting of OSM, HGF, dexamethasone, nicotinamide, dimethyl sulfoxide, and sodium butyrate.

16. A pancreatic cell production method comprising the step of:
differentiating endodermal cells into pancreatic cells in the presence of a pancreatic cell differentiation factor,
wherein the endodermal cells are obtained by the endodermal cell production method according to claim 1.

17. The endodermal cell production method according to claim 1, wherein
the endodermal cell inducing factor comprises a TGF-β family protein and a PI$_3$K protein activity inhibitory compound, or comprises a TGF-β family protein, a PI$_3$K protein activity inhibitory compound, and a GSK-3β protein activity inhibitory compound.

18. The endodermal cell production method according to claim 1, wherein
the inducing step is a step of inducing differentiation of the pluripotent cells into the endodermal cells in the presence of a culture solution containing the endodermal cell inducing factor,
in the inducing step, the ROCK protein activity is inhibited by a ROCK protein activity inhibitory compound, and
the culture solution contains a TGF-β family protein, a PI$_3$K protein activity inhibitory compound, a GSK-3β protein activity inhibitory compound, bFGF, and insulin.

19. The endodermal cell production method according to claim 17, wherein
the TGF-β family protein comprises activin A and BMP-4.

20. The endodermal cell production method according to claim 1, wherein
in the inducing step, the ROCK protein activity is inhibited by a ROCK protein activity inhibitory compound,
the inducing step is a step of inducing differentiation of the pluripotent cells into the endodermal cells in the presence of a first culture solution, a second culture solution, and a third culture solution, each containing the endodermal cell inducing factor,
the first culture solution contains activin A and the ROCK protein activity inhibitory compound,
the second culture solution contains activin A, BMP-4, a PI$_3$K protein activity inhibitory compound, a GSK-3β protein activity inhibitory compound, and the ROCK protein activity inhibitory compound,
the third culture solution contains activin A, BMP-4, a PI$_3$K protein activity inhibitory compound, and the ROCK protein activity inhibitory compound, and
the inducing step comprises:
a first step of culturing the pluripotent cells in the presence of the first culture solution;
a second step of culturing cells obtained in the first step in the presence of the second culture solution; and
a third step of culturing cells obtained in the second step in the presence of the third culture solution.

* * * * *